US009404112B2

(12) United States Patent
Gryaznov et al.

(10) Patent No.: US 9,404,112 B2
(45) Date of Patent: Aug. 2, 2016

(54) MODIFIED OLIGONUCLEOTIDES FOR TELOMERASE INHIBITION

(75) Inventors: Sergei Gryaznov, San Mateo, CA (US); Krisztina Pongracz, Oakland, CA (US)

(73) Assignee: Geron Corporation, Menlo Park, CA (US)

( * ) Notice: Subject to any disclaimer, the term of this patent is extended or adjusted under 35 U.S.C. 154(b) by 450 days.

(21) Appl. No.: 13/590,511

(22) Filed: Aug. 21, 2012

(65) Prior Publication Data
US 2013/0065950 A1 Mar. 14, 2013

Related U.S. Application Data

(63) Continuation of application No. 12/886,080, filed on Sep. 20, 2010, now abandoned, which is a continuation of application No. 12/276,127, filed on Nov. 21, 2008, now abandoned, which is a continuation of application No. 10/938,184, filed on Sep. 9, 2004, now Pat. No. 7,494,982.

(60) Provisional application No. 60/501,509, filed on Sep. 9, 2003.

(51) Int. Cl.
*C12N 15/113* (2010.01)
*A61K 31/7088* (2006.01)
*A61K 47/48* (2006.01)

(52) U.S. Cl.
CPC ...... *C12N 15/1137* (2013.01); *A61K 47/48038* (2013.01); *A61K 47/48053* (2013.01); *C12N 2310/113* (2013.01); *C12N 2310/314* (2013.01); *C12N 2310/3515* (2013.01); *C12N 2320/30* (2013.01); *C12Y 207/07049* (2013.01)

(58) Field of Classification Search
CPC ............ A61K 39/00; A61K 47/48238; A61K 47/48907; A61K 47/48915; A61K 9/5123; A61K 9/5153; A61K 9/5192; A61K 2039/53; A61K 31/7105; A61K 31/711; A61K 38/16; A61K 48/00; A61K 48/0058; B82Y 5/00
USPC ....... 514/1.1, 44 R, 44 A, 178, 182; 435/325, 435/375; 424/184.1, 422, 450, 484
See application file for complete search history.

(56) References Cited

U.S. PATENT DOCUMENTS

| | | | |
|---|---|---|---|
| 4,659,774 A | 4/1987 | Webb et al. | |
| 4,757,141 A | 7/1988 | Fung et al. | |
| 4,904,582 A | 2/1990 | Tullis | |
| 4,958,013 A | 9/1990 | Letsinger | |
| 5,185,444 A | 2/1993 | Summerton et al. | |
| 5,411,947 A | 5/1995 | Hostetler et al. | |
| 5,416,203 A | 5/1995 | Letsinger | |
| 5,420,330 A | 5/1995 | Brush | |
| 5,476,925 A | 12/1995 | Letsinger et al. | |
| 5,563,050 A | 10/1996 | Peyman et al. | |
| 5,591,607 A | 1/1997 | Gryaznov et al. | |
| 5,599,922 A | 2/1997 | Gryaznov et al. | |
| 5,631,135 A | 5/1997 | Gryaznov et al. | |
| 5,646,260 A | 7/1997 | Letsinger et al. | |
| 5,648,480 A | 7/1997 | Letsinger et al. | |
| 5,684,143 A | 11/1997 | Gryaznov et al. | |
| 5,726,297 A | 3/1998 | Gryaznov et al. | |
| 5,763,208 A | 6/1998 | Bischofberger et al. | |
| 5,824,793 A | 10/1998 | Hirschbein et al. | |
| 5,837,694 A | 11/1998 | Barrett | |
| 5,837,835 A | 11/1998 | Gryaznov et al. | |
| 5,846,723 A | 12/1998 | Kim et al. | |
| 5,856,461 A | 1/1999 | Colote et al. | |
| 5,859,233 A | 1/1999 | Hirschbein et al. | |
| 5,932,718 A | 8/1999 | Letsinger et al. | |
| 5,952,490 A | 9/1999 | Hanecak et al. | |
| 5,965,720 A | 10/1999 | Gryaznov et al. | |
| 5,998,604 A | 12/1999 | Fearon et al. | |
| 6,001,991 A | 12/1999 | Dean et al. | |
| 6,015,710 A | 1/2000 | Shay et al. | |
| 6,153,737 A | 11/2000 | Manoharan et al. | |
| 6,166,188 A | 12/2000 | Cook et al. | |
| 6,169,170 B1 | 1/2001 | Gryaznov et al. | |
| 6,221,850 B1 | 4/2001 | McKay et al. | |
| 6,235,886 B1 | 5/2001 | Manoharan et al. | |
| 6,265,558 B1 | 7/2001 | Cook et al. | |
| 6,350,853 B1 | 2/2002 | Nielsen et al. | |
| 6,395,492 B1 | 5/2002 | Manoharan et al. | |
| 6,448,392 B1 | 9/2002 | Hostetlet et al. | |
| 6,608,036 B1 | 8/2003 | Gryaznov et al. | |
| 6,683,826 B1 | 1/2004 | Matsuo et al. | |
| 6,762,169 B1 | 7/2004 | Manoharan | |
| 6,835,826 B2 | 12/2004 | Gryaznov et al. | |
| 7,067,497 B2 | 6/2006 | Hanecak et al. | |
| 7,138,383 B2 | 11/2006 | Gryaznov et al. | |
| 7,485,717 B2 | 2/2009 | Gryaznov et al. | |
| 7,494,982 B2 * | 2/2009 | Gryaznov et al. | ........... 514/44 R |

(Continued)

FOREIGN PATENT DOCUMENTS

JP 2003-513887 4/2003
WO WO 90/10448 A1 9/1990

(Continued)

OTHER PUBLICATIONS

Herbert et al., "Inhibition of human telomerase in immortal human cells leads to progressive telomere shortening and cell death", *Proc. Natl. Acad. Sci. USA* 96(25):14276-81 (Dec. 7, 1999).

(Continued)

*Primary Examiner* — Janet Epps-Smith
(74) *Attorney, Agent, or Firm* — Carol L. Francis; Glenn J. Foulds; Bozicevic, Field & Francis LLP

(57) ABSTRACT

Compounds comprising an oligonucleotide moiety covalently linked to a lipid moiety are disclosed. The oligonucleotide moiety comprises a sequence that is complementary to the RNA component of human telomerase. The compounds inhibit telomerase activity in cells with a high potency and have superior cellular uptake characteristics.

15 Claims, 17 Drawing Sheets

(56) References Cited

U.S. PATENT DOCUMENTS

| | | |
|---|---|---|
| 7,563,618 B2 | 7/2009 | Gryaznov et al. |
| 8,748,593 B2 | 6/2014 | Gryaznov et al. |
| 2003/0138814 A1 | 7/2003 | Gryaznov et al. |
| 2007/0015723 A1 | 1/2007 | Hanecak et al. |
| 2007/0037770 A1 | 2/2007 | Gryaznov et al. |
| 2007/0270363 A1 | 11/2007 | Bennett et al. |
| 2009/0286853 A1 | 11/2009 | Gryaznov et al. |
| 2012/0129918 A1 | 5/2012 | Gryaznov et al. |
| 2012/0329858 A1 | 12/2012 | Gryaznov et al. |
| 2013/0065950 A1 | 3/2013 | Gryaznov et al. |
| 2014/0349292 A1 | 11/2014 | Gryaznov et al. |

FOREIGN PATENT DOCUMENTS

| | | |
|---|---|---|
| WO | WO 91/14696 | 10/1991 |
| WO | WO 94/08053 A1 | 4/1994 |
| WO | WO 95/25814 | 9/1995 |
| WO | WO 96/01835 A1 | 1/1996 |
| WO | WO 96/14277 | 5/1996 |
| WO | WO 97/31009 | 8/1997 |
| WO | WO 97/37691 A1 | 10/1997 |
| WO | WO 97/38013 A1 | 10/1997 |
| WO | WO 98/28442 | 7/1998 |
| WO | WO 01/18015 | 3/2001 |
| WO | WO 01/18015 A1 | 3/2001 |
| WO | WO 02/077184 | 10/2002 |
| WO | WO 2004/029277 A2 | 4/2004 |
| WO | WO 2005/023994 | 3/2005 |
| WO | WO 2006/014387 | 2/2006 |

OTHER PUBLICATIONS

Asai et al., *Cancer Res.*, 63:3931-3939 (2003).
Nelson et al., *Nucleic Acids Research*, 20(23):6253-6259 (1992).
Pruzan et al., *Nucleic Acids Research*, 30(2):559-568 (2002).
Shea et al., *Nucleic Acids Research*, 18(13):3777-3783 (1990).
Crooke et al., *The Journal of Pharmacology and Exp. Res.*, 277(2):923-937 (1996).
Fiedler et al., *Langenbeck's Arch. Surg.*, 383:269-275 (1998).
Gerster et al., *Analytical Biochemistry*, 262:177-184 (1998).
Gryaznov and Lloyd, *Nucleic Acids Research*, 21:5909-5915 (1993).
MacKellar et al., *Nucleic Acids Res.*, 20(13):3411-3417 (1992).
Manoharan, M., *Antisense and Nucleic Drug Dev.*, 12:103-128 (2002).
Manoharan et al., *Bioorg. Med. Chem.*, 4(8):1053-1060 (2002).
Mishra et al., *Biochimica et Biophysica ACTA*, 1264:229-237 (1995).
Saison-Behmoaras et al., *The Embo Journal*, 10(5):1111-1118 (1991).
Will et al., *Tetrahedron Letters*, 33(19):2729-2732 (1992).
Shea-Herbert et al., *Oncogene*, 21, 638-642 (2002).
Schirmeister-Techy et al., *Helvetica Chimica Acta.*, vol. 82, 597-613 (1999).
C.A. Stein, *Pharmacology & Therapeutics*, vol. 85, 231-236 (2000).
Jen et al., *Stem Cells*, vol. 18, 307-319 (2000).
Chirilia et al., *Biomaterials*, vol. 23, 321-342 (2002).
Office Action mailed Aug. 28, 2008, U.S. Appl. No. 10/255,535, filed Sep. 25, 2002.
Office Action mailed Jan. 8, 2008, U.S. Appl. No. 10/255,535, filed Sep. 25, 2002.
Office Action mailed May 15, 2007, U.S. Appl. No. 10/255,535, filed Sep. 25, 2002.
Office Action mailed Sep. 8, 2006, U.S. Appl. No. 10/255,535, filed Sep. 25, 2002.
Office Action mailed Aug. 29, 2008, U.S. Appl. No. 10/255,535, filed Sep. 25, 2002.
"Cancer [online], [retrieved on Jul. 6, 2007] Retrieved from the Internet, URL: http://www.nlm.nih.gov/medlineplus/cancer.html".
Golub, et al., "Molecular Classification of Cancer: Class Discovery and Class Prediction by Gene Expression Monitoring", Science (1999), vol. 286, 531-537, 1999, 531-537.
Lala, et al., "Role of Nitric Oxide in Tumor Progression: Lessons from Experimental Tumors", Cancer and Metastasis Reviews (1998), 17, 91-106, 1998, 91-106.
Brian R. Keppler et al., "inhibition of Telomerase Activity by Preventing Proper Assemblage", *Biochemistry* 43, pp. 334-343 (2004).
U.S. Appl. No. 14/714,732, filed May 18, 2015, Gryaznov et al.
U.S. Appl. No. 14/720,466, filed May 22, 2015, Gryaznov et al.
U.S. Appl. No. 14/720,467, filed May 22, 2015, Gryaznov et al.
Baraniak, J. et al., "New approach to solid phase synthesis of N3'-P5'phosphoramidate oligonucleotides", Nucleosides & Nucleotides 17(8), 1998, 1347-53.
Chapuis, H. et al., "Shorter puromycin analog synthesis by means of an efficient Staudinger-Vilarrasa coupling", Tetrahedron 62, 2006, pp. 12108-12115.
Chur, Anette et al., "Synthesis of a carboxamide linked T*T dimer and its incorporation in oligonucleotides", Nucleic Acids Research, vol. 21, No. 22, 1993, 5179-5183.
Demirtas, Turk , "The Selective Protection and Deprotection of Ambident Nucleophiles with Parent and Substituted Triarylmethyls", J Chem 26, 2002, 889-896.
Dong, "Solid-Phase Synthesis of Dipeptide-Conjugated Nucleosides and Their Interaction with RNA", Helvetica Chimica Acta vol. 86, 2003, 3516-3524.
Fields, "Peptide Synthesis Protocols", Methods in Molecular Biology, vol. 35, Chapter 2, 1994.
Froehler, B. et al., "Dialkylformamidines: depurination resistant N6-protecting group for deoxyadenosine", Nucl. Acids Res. 11(22), 1983, 8031-8036.
Gaytan, Paul et al., "Combination of DMT-mononucleotide and Fmoc-trinucleotide phosphoramidites in oligonucleotide synthesis affords an automatable codon-level mutagenesis method", Chemistry & Biology, vol. 5, No. 9, 1998, 519-527.
Goodnow, "Synthesis of Thymine, Cytosine, Adenine, and Guanine Containing N-Fmoc Protected Amino Acids: Building Blocks for Construction of Novel Oligonucleotide Backbone Analogs", Tetrahedron Letters, vol. 38, No. 18, 1997, 3195-3198.
Greene, T. et al., Protective Groups in Organic Synthesis, Third Edition, John Wiley & Sons, Inc., New York, 1999, p. 588.
Greene, T. et al., "Protection for the hydroxyl group, including 1,2- and 1,3-diols", Protective Groups in Organic Synthesis, Third Edition, John Wiley & Sons, Inc., New York, 1999, pp. 17-23, 494-502.
Greene, T. et al., "Protective Groups in Organic Synthesis", John Wiley & Sons, Inc., New York, 1999, pp. 4-5,119,142-143, 513, 550, 559, 583-584.
Gryaznov, S. et al., "RNA mimetics: oligoribonucleotide N3'-P5' phosphoramidates", Nucl. Acids Res. 26(18), 1998, pp. 4160-4167.
Hassler, Matthew et al., "RNA synthesis via dimer and trimer phosphoramidite block coupling", Tetrahedron Letters 52, 2011, 2575-2578.
Herdering, Wilhelm et al., "Phosphoramidites of Chiral (Rp)- and (Sp)-Configurated d(T[P-180]-A): Synthesis, Configurational Assignment, and Use as Dimer Blocks in Oligonucleotide Synthesis", Helvetica Chimica Acta vol. 68, 1985, 2119-2127.
Iyer, et al., "The automated synthesis of sulfur-containing oligodeoxyribonucleotides using 3H-1,2-benzodithiol-3-one 1, 1-dioxide as a sulfur-transfer reagent", J. Org. Chem. 55 (15), 1990, 4693-4699.
Iyer, R. et al., "3H-1,2-benzodithiole-3-one 1,1-dioxide as an improved sulfurizing reagent in the solid-phase synthesis of oligodeoxyribonucleoside phosphothiorates", J. Am. Chem. Soc. 112, 1990, 1253-1254.
Kates, S. et al., Solid-Phase Synthesis: A Practical Guide, Marcel-Dekker, Inc., New York, 2000, pp. 478-480.
Liekens, S. et al., "The nucleoside derivative 5'-O-trityl-inosine (KIN59) suppresses thymidine phosphorylase-triggered angiogenesis via a noncompetitive mechanism of action", J. Biol. Chem. 279(28), 2004, pp. 29598-295605.
Matray, T. et al., "Synthesis and properties of RNA analogs—oligoribonucleotide N3'-P5' phosphoramidates", Nucl. Acids Res. 27(20), 1999, pp. 3976-3985.
McCurdy, S. et al., "An Improved Method for the Synthesis of N3'->P5' Phosphoramidate Oligonucleotides", Tetrahedron Lett. 38(2), (1997), pp. 207-210.

(56) References Cited

OTHER PUBLICATIONS

Mignet, N. et al., "Zwitterionic Oligodeoxyribonucleotide N3'—>P5' Phosphoramidates: Synthesis and Properties", Nucl. Acids Res. 26(2), 1998, 431-438.

Nakajima, K. et al., "Studies on Aziridine-2-carboxylic Acid. I. Synthesis of the Optically Active L-Aziridine-2-carboxylic Acid and Its Derivatives", Bull. Chem. Soc. Jpn. 51, 1978, 1577-1578.

Nelson, J. et al., "N3'-P5' oligodeoxyribonucleotide phosphoramidates: a new method of synthesis based on a phosphoramidate amine-exchange reaction", J. Org. Chem. 62, 1997, pp. 7278-7287.

Ohkubo, et al., Org. Lett. 12 (11), 2010, 2496-2499.

Ono, Akira et al., "The synthesis of blocked triplet-phosphoramidites and their use in mutagenesis", Nucleic Acids Research, vol. 23, No. 22, 1995, 4677-4682.

Pongracz, K. et al., "Alpha-Oligodeoxyribonucleotide N3'—>P5' phosphoramidates: synthesis and duplex formation", Nucl. Acids Res. 26(4), 1998, 1099-106.

Pongracz, K. et al., "Oligonucleotide N3'—>P5' thiophosphoramidates: synthesis and properties", Tetrahedron Lett. 40, 1999, pp. 7661-7664.

Ti, G. et al., "Transient protection: efficient one-flask syntheses of protected deoxynucleosides", J. Am. Chem. Soc. 104, 1982, pp. 1316-1319.

Zhang, B. et al., "Synthesis of pCpCpA-3'-NH-phenylalanine as a ribosomal substrate", Organic Lett. 4(21), 2002, pp. 3615-3618.

Zhang, Lei et al., "An efficient synthesis of 3'-amino-3'-deoxyguanosine from guanosine", Helvetica Chimica Acta 86, 2003, 703-710.

\* cited by examiner

FIG. 1
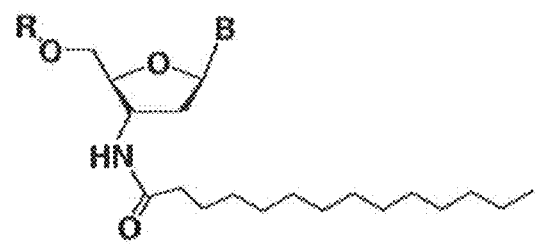
FIG. 1A
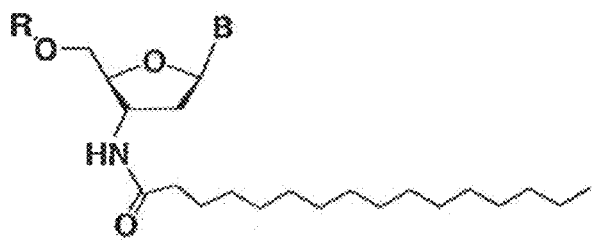
FIG. 1B
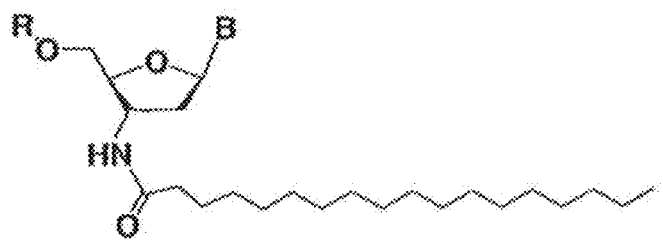
FIG. 1C
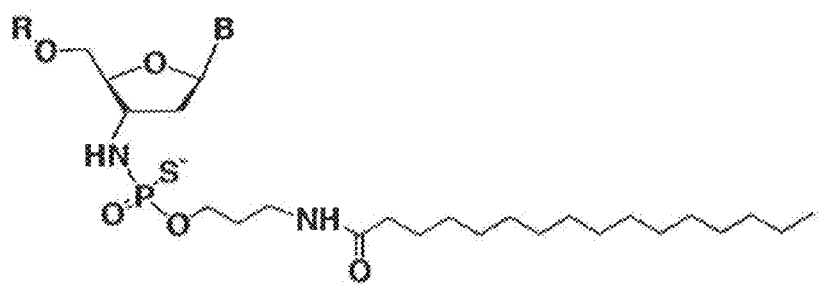
FIG. 1D

FIG. 2
FIG. 2A
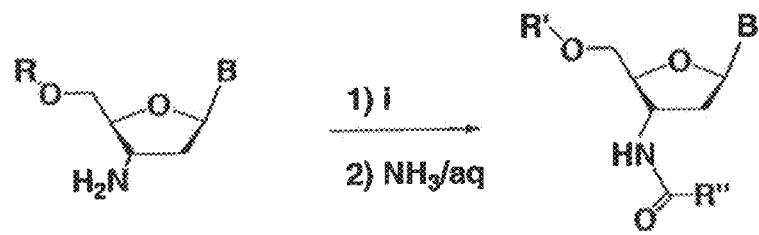
FIG. 2B
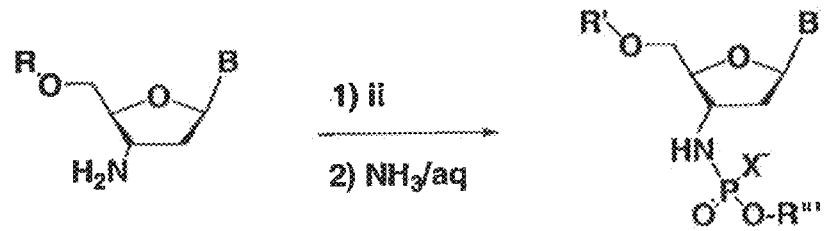
FIG. 2C
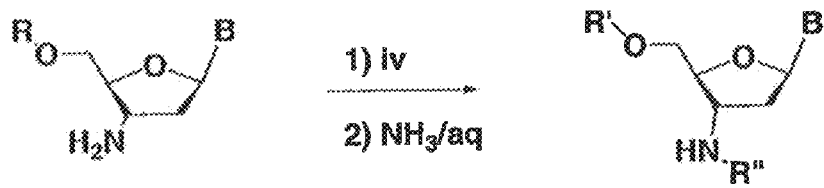

FIG. 9
TAGGGTTAGACAA            Fig. 9A
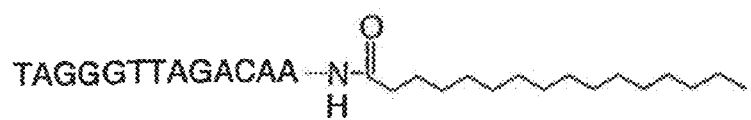
Fig. 9B
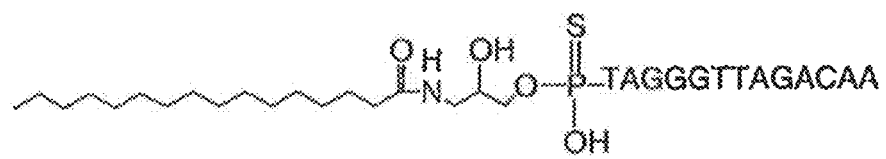
Fig. 9C

SEQUENCE LISTING

<160> NUMBER OF SEQ ID NOS: 21

<210> SEQ ID NO 1
<211> LENGTH: 451
<212> TYPE: RNA
<213> ORGANISM: Hom sapiens

<400> SEQUENCE: 1

```
ggguugcgga ggguggggccu gggaggggug guggccauuu uuugucuaac ccuaacugag    60
aagggcguag gcgccgugcu uuugcucccc gcgcgcuguu uuucucgcug acuuucagcg   120
ggcggaaaag ccucggccug ccgccuucca ccguucauuc uagagcaaac aaaaaaugac   180
agcugcuggc ccguucgccc cucccgggga ccugcggcgg gucgccugcc cagccccga    240 accccgccug gaggccgcgg ucggcccggg gcuucuccgg aggcacccac ugccaccgcg   300
aagaguuggg cucugucagc cgcgggucuc ucggggcga gggcgagguu caggccuuuc    360
aggccgcagg aagaggaacg gagcgagucc ccgcgcgcgg cgcgauuccc ugagcugugg   420
gacgugcacc caggacucgg cucacacaug c                                  451
```

<210> SEQ ID NO 2
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 2

```
gctctagaat gaacggtgga aggcggcagg                                     30
```

<210> SEQ ID NO 3
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 3

```
gtggaaggcg gcagg                                                     15
```

<210> SEQ ID NO 4
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 4

```
ggaaggcggc agg                                                       13
```

<210> SEQ ID NO 5
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 5

```
gtggaaggcg gca                                                       13
```

<210> SEQ ID NO 6
<211> LENGTH: 11
<212> TYPE: DNA
<213> ORGANISM: Artificial Sequence

```
<220> FEATURE:
<223> OTHER INFORMATION: Synthetic oligonucleotide

<400> SEQUENCE: 6
gtggaaggcg g                                                          11

<210> SEQ ID NO 7
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 7
cggtggaagg cgg                                                        13

<210> SEQ ID NO 8
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 8
acggtggaag gcg                                                        13

<210> SEQ ID NO 9
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 9
aacggtggaa ggcggc                                                     16

<210> SEQ ID NO 10
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 10
atgaacggtg gaaggcgg                                                   18

<210> SEQ ID NO 11
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 11
acattttttg tttgctctag                                                 20

<210> SEQ ID NO 12
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 12
tagggttaga caa                                                        13
```

```
<210> SEQ ID NO 13
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 13
gttagggtta g                                                            11

<210> SEQ ID NO 14
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 14
gttagggtta gac                                                          13

<210> SEQ ID NO 15
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 15
gttagggtta gacaa                                                        15

<210> SEQ ID NO 16
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 16 gggttagac                                                                9

<210> SEQ ID NO 17
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 17 cagttaggg                                                                9

<210> SEQ ID NO 18
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 18
cccttctcag tt                                                           12

<210> SEQ ID NO 19
<211> LENGTH: 12
<212> TYPE: DNA
<213> ORGANISM: Artificial Sequence
<220> FEATURE:
<223> OTHER INFORMATION: Synthetic oligonucleotide
```

```
<400> SEQUENCE: 19
cgcccttctc ag                                                    12

<210> SEQ ID NO 20
<211> LENGTH: 11
<212> TYPE: RNA
<213> ORGANISM: Homo sapiens

<400> SEQUENCE: 20
cuaacccuaa c                                                     11

<210> SEQ ID NO 21
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 21
cagttagggt tag                                                   13
```

MODIFIED OLIGONUCLEOTIDES FOR TELOMERASE INHIBITION

This is a continuation of application Ser. No. 12/886,080, filed Sep. 20, 2010, which is a continuation of application Ser. No. 12/276,127, filed Nov. 21, 2008, which is a continuation of application Ser. No. 10/938,184, filed Sep. 9, 2004, which claims the benefit of Provisional Application No. 60/501,509, filed Sep. 9, 2003.

REFERENCE TO RELATED APPLICATIONS

This disclosure claims the priority benefit of U.S. provisional application 60/501,509, filed Sep. 9, 2003. The priority application is hereby incorporated herein by reference in its entirety.

TECHNICAL FIELD

This invention relates to compounds useful for the inhibition of telomerase. More specifically, the invention provides modified oligonucleotides that are targeted to the RNA component of telomerase and have enhanced cellular uptake characteristics.

BACKGROUND

Development of Oligonucleotides for Therapeutic Applications

There is much interest in the medical uses of nucleic acids. For example, antisense, ribozymes, aptamer and RNA interference (RNAi) technologies are all being developed for potential therapeutic applications. The design of nucleic acids, particularly oligonucleotides, for in vivo delivery requires consideration of various factors including binding strength, target specificity, serum stability, resistance to nucleases and cellular uptake. A number of approaches have been proposed in order to produce oligonucleotides that have characteristics suitable for in vivo use, such as modified backbone chemistry, formulation in delivery vehicles and conjugation to various other moieties. Therapeutic oligonucleotides with characteristics suitable for systemic delivery would be particularly beneficial.

Oligonucleotides with modified chemical backbones are reviewed in Micklefield, Backbone modification of nucleic acids: synthesis, structure and therapeutic applications, Curr. Med. Chem., 8 (10):1157-79, 2001 and Lyer et al., Modified oligonucleotides—synthesis, properties and applications, Curr. Opin. Mol. Ther., 1 (3): 344-358, 1999.

Examples of modified backbone chemistries include:
peptide nucleic acids (PNAs) (see Nielsen, Methods Mol. Biol., 208:3-26, 2002),
locked nucleic acids (LNAs) (see Peterson & Wengel, Trends Biotechnol., 21 (2):74-81, 2003),
phosphorothioates (see Eckstein, Antisense Nucleic Acid Drug Dev., 10 (2):117-21, 2000),
methylphosphonates (see Thiviyanathan et al., Biochemistry, 41 (3):827-38, 2002),
phosphoramidates (see Gryaznov, Biochem. Biophys. Acta, 1489 (1):131-40, 1999; Pruzan et al., Nucleic Acids Res., 30 (2):559-68, 2002), and
thiophosphoramidates (see Gryaznov et al., Nucleosides Nucleotides Nucleic Acids, 20 (4-7):401-10, 2001; Herbert et al., Oncogene, 21 (4):638-42, 2002).

Each of these types of oligonucleotides has reported advantages and disadvantages. For example, peptide nucleic acids (PNAs) display good nuclease resistance and binding strength, but have reduced cellular uptake in test cultures; phosphorothioates display good nuclease resistance and solubility, but are typically synthesized as P-chiral mixtures and display several sequence-non-specific biological effects; methylphosphonates display good nuclease resistance and cellular uptake, but are also typically synthesized as P-chiral mixtures and have reduced duplex stability. The N3'→P5' phosphoramidate internucleoside linkages are reported to display favorable binding properties, nuclease resistance, and solubility (Gryaznov and Letsinger, Nucleic Acids Research, 20:3403-3409, 1992; Chen et al., Nucleic Acids Research, 23:2661-2668, 1995; Gryaznov et al., Proc. Natl. Acad. Sci., 92:5798-5802, 1995; Skorski et al., Proc. Natl. Acad. Sci., 94:3966-3971, 1997). However, they also show increased acid lability relative to the natural phosphodiester counterparts (Gryaznov et al., Nucleic Acids Research, 24:1508-1514, 1996). Acid stability of an oligonucleotide is an important quality given the desire to use oligonucleotide agents as oral therapeutics. The addition of a sulfur atom to the backbone in N3'→P5' thiophosphoramidate oligonucleotides provides enhanced acid stability.

As with many other therapeutic compounds, the polyanionic nature of oligonucleotides reduces the ability of the compound to cross lipid membranes, limiting the efficiency of cellular uptake. Various solutions have been proposed for increasing the cellular uptake of therapeutic agents, including formulation in liposomes (for reviews, see Pedroso de Lima et al., Curr Med Chem, 10 (14):1221-1231, 2003 and Miller, Curr Med Chem., 10 (14):1195-211, 2003) and conjugation with a lipophilic moiety. Examples of the latter approach include: U.S. Pat. No. 5,411,947 (Method of converting a drug to an orally available form by covalently bonding a lipid to the drug); U.S. Pat. No. 6,448,392 (Lipid derivatives of antiviral nucleosides: liposomal incorporation and method of use); U.S. Pat. No. 5,420,330 (Lipo-phosphoramidites); U.S. Pat. No. 5,763,208 (Oligonucleotides and their analogs capable of passive cell membrane permeation); Gryaznov & Lloyd, Nucleic Acids Research, 21:5909-5915, 1993 (Cholesterol-conjugated oligonucleotides); U.S. Pat. No. 5,416,203 (Steroid modified oligonucleotides); WO 90/10448 (Covalent conjugates of lipid and oligonucleotide); Gerster et al., Analytical Biochemistry, 262:177-184 (1998) (Quantitative analysis of modified antisense oligonucleotides in biological fluids using cationic nanoparticles for solid-phase extraction); Bennett et al., Mol. Pharmacol., 41:1023-1033 (1992) (Cationic lipids enhance cellular uptake and activity of phosphorothioate antisense oligonucleotides); Manoharan et al., Antisense and Nucleic Acid Drug Dev., 12:103-128 (2002) (Oligonucleotide conjugates as potential antisense drugs with improved uptake, biodistribution, targeted delivery and mechanism of action); and Fiedler et al., Langenbeck's Arch. Surg., 383:269-275 (1998) (Growth inhibition of pancreatic tumor cells by modified antisense oligodeoxynucleotides).

Telomerase as a Therapeutic Target

Telomerase is a ribonucleoprotein that catalyzes the addition of telomeric repeat sequences to chromosome ends. See Blackburn, 1992, Ann. Rev. Biochem., 61:113-129. There is an extensive body of literature describing the connection between telomeres, telomerase, cellular senescence and cancer (for a general review, see Oncogene, volume 21, January 2002, which is an entire issue of the journal focused on telomerase). Telomerase has therefore been identified as an excellent target for cancer therapeutic agents (see Lichsteiner et al., Annals New York Acad. Sci., 886:1-11, 1999).

Genes encoding both the protein and RNA components of human telomerase have been cloned and sequenced (see U.S. Pat. Nos. 6,261,836 and 5,583,016, respectively) and much effort has been spent in the search for telomerase inhibitors. Telomerase inhibitors identified to date include small molecule compounds and oligonucleotides. Various publications describe the use of oligonucleotides to inhibit telomerase, either targeted against the mRNA encoding the telomerase protein component (the human form of which is known as human telomerase reverse transcriptase or hTERT) or the RNA component of the telomerase holoenzyme (the human form of which is known as human telomerase RNA or hTR). Oligonucleotides that are targeted to the hTERT mRNA are generally believed to act as conventional antisense drugs in that they bind to the mRNA, resulting in destruction of the mRNA, and thereby preventing production of the hTERT protein (see, for example, U.S. Pat. No. 6,444,650). Certain oligonucleotides that are targeted to hTR are designed to bind to hTR molecules present within the telomerase holoenzyme, and thereby disrupt enzyme function (see, for example, U.S. Pat. No. 6,548,298). Examples of publications describing various oligonucleotides designed to reduce or eliminate telomerase activity include:

U.S. Pat. No. 6,444,650 (Antisense compositions for detecting and inhibiting telomerase reverse transcriptase);

U.S. Pat. No. 6,331,399 (Antisense inhibition of tert expression);

U.S. Pat. No. 6,548,298 (Mammalian telomerase);

Van Janta-Lipinski et al., Nucleosides Nucleotides, 18 (6-7):1719-20, 1999 (Protein and RNA of human telomerase as targets for modified oligonucleotides);

Gryaznov et al., Nucleosides Nucleotides Nucleic Acids, 20: 401-410, 2001 (Telomerase inhibitors-oligonucleotide phosphoramidates as potential therapeutic agents);

Herbert et al., Oncogene, 21 (4):638-42, 2002 (Oligonucleotide phosphoramidates as efficient telomerase inhibitors);

Pruzan et al., Nucleic Acids Research, 30 (2):559-568, 2002 (Allosteric inhibitors of telomerase: oligonucleotide N3'-P5' phosphoramidates);

PCT publication WO 01/18015 (Oligonucleotide N3'-P5' thiophosphoramidates: their synthesis and use); and Asai et al., Cancer Research, 63:3931-3939, 2003 (A novel telomerase template antagonist (GRN163) as a potential anticancer agent).

SUMMARY OF THE INVENTION

The compositions and methods of the present invention relate to telomerase inhibiting compounds comprising an oligonucleotide and at least one covalently linked lipid group. The compounds of the invention have superior cellular uptake properties compared to unmodified oligonucleotides. This means that an equivalent biological effect may be obtained using smaller amounts of the conjugated oligonucleotide compared to the unmodified form. When applied to the human therapeutic setting, this may translate to reduced toxicity risks, and cost savings. The compounds of the invention inhibit telomerase in cells, including cancer cells, the resultant effect of which is to inhibit proliferation of the cells. Accordingly, a primary application of the compounds of the invention is as cancer therapeutics, and the invention provides pharmaceutical formulations of the compounds that may be utilized in this manner.

The compounds of the invention may be represented by the formula:

$$O\text{-}(x\text{-}L)_n,$$

where O represents the oligonucleotide, x is an optional linker group, L represents the lipid moiety and n is an integer from 1-5. Typically, n=1 or 2, but where n>1, each lipid moiety L is independently selected. The lipid moiety is typically covalently attached to the oligonucleotide at one (or if n=2, each) of the 3' and 5' termini, but may also be attached at other sites, including one or more bases.

The lipid group L is typically an aliphatic hydrocarbon or fatty acid, including derivatives of hydrocarbons and fatty acids, with examples being saturated straight chain compounds having 14-20 carbons, such as myristic acid (C14, also known as tetradecanoic acid), palmitic acid (C16, also known as hexadecanoic acid) and stearic acid (C18, also known as octadeacanoic acid), and their corresponding aliphatic hydrocarbon forms, tetradecane, hexadecane and octadecane, together with derivatives such as amine and amide derivatives. Examples of other suitable lipid groups that may be employed are sterols, such as cholesterol, and substituted fatty acids and hydrocarbons, particularly poly-fluorinated forms of these groups. The oligonucleotide component O can be a ribo- or deoxyribonucleic acid or modified forms thereof, and the linkages connecting the nucleobases may be made with any compatible chemistry, including, but not limited to: phosphodiester; phosphotriester; methylphosphonate; phosphoramidate; N3'→P5' phosphoramidate; N3'→P5' thiophosphoramidate; and phosphorothioate linkages. N3'→P5' phosphoramidate and N3'→P5' thiophosphoramidate chemistries are preferred. The sequence of the oligonucleotide component O includes at least one sequence region that is complementary, preferably exactly complementary, to a selected "target" region of the sequence of the telomerase RNA component. In particular embodiments, the sequence of the oligonucleotide component O contains a sequence region that is complementary to sequence within one of the following regions of the human telomerase RNA component, hTR (the sequence of which is provided in SEQ ID NO:1): 46-56, 137-196, 290-319, and 350-380. The length of sequence within the O component that is exactly complementary to a region of hTR is preferably at least 5 bases, more preferably at least 8 bases, and still more preferably at least 10 bases. Additional sequence regions may be added to the O component that are not exactly complementary to hTR, but which may provide an additional beneficial function.

Exemplary compounds of the invention include those depicted in the structures below in which the O component has N3'→P5' thiophosphoramidate inter-nucleoside linkages and is exactly complementary to bases 42-54 of hTR (SEQ ID NO:1). In the first exemplary structure, L, the lipid moiety is palmitoyl amide (derived from palmitic acid), conjugated through an aminoglycerol linker to the 5' thiophosphate group of the oligonucleotide O:

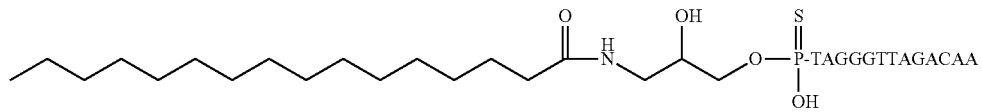

In the second exemplary structure, L is conjugated through the 3' amino group of the oligonucleotide to palmitoyl amide:

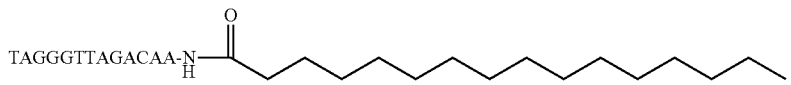

Compounds of the invention, including these exemplary compounds, are shown to have superior cellular uptake properties, compared to corresponding unmodified oligonucleotides, and therefore to be more effective inhibitors of cellular telomerase activity. As a consequence of these properties, compounds of the invention are highly effective inhibitors of cancer cell proliferation.

The compounds of the present invention may be used in methods to inhibit telomerase enzymatic activity. Such methods comprise contacting a telomerase enzyme with a compound of the invention. The compounds of the present invention may also be used to inhibit telomerase in cells that express telomerase, thereby inhibiting the proliferation of such cells. Such methods comprise contacting a cell or cells having telomerase activity with a compound of the invention. Cells treated in this manner, which may be cells in vitro, or cells in vivo, will generally undergo telomere shortening and cease proliferating. Since cancer cells require telomerase activity for long-term proliferation, the compounds of the invention are particularly useful for inhibiting the growth of cancer cells, and may be used in therapeutic applications to treat cancer.

Aspects of the invention therefore include the compounds as described herein for use in medicine, and in particular for use in treating cancer.

Also provided herein are pharmaceutical compositions comprising an oligonucleotide conjugate according to the invention formulated with a pharmaceutically acceptable excipient.

BRIEF DESCRIPTION OF THE DRAWINGS

FIG. 2 shows schematics of exemplary synthesis procedures for the compounds of the invention. FIGS. 2A, 2B and 2C show synthesis procedures that may be used for the production of compounds in which the lipid moiety is conjugated to the 3' terminus of the oligonucleotide. The scheme shown in FIG. 2C is a reductive amination starting with a lipid aldehyde; this produces an amine linkage between the lipid group and the oligonucleotide (see Schematic B below), in contrast to the scheme shown in FIG. 2A where the starting materials are carboxylic acid, acid anhydride or acid chloride forms of a fatty acid, resulting in the formation of an amide linkage (see Schematic A below). FIG. 2B shows a scheme suitable for producing a 3'-thiophosphoramidate linkage. In this example, an amino glycerol linker sequence (O—CH2CH2CH2-NHC(O))— is shown, but it will be appreciated that this synthesis may be employed without such a linker, or with alternative linker sequences. In FIG. 2, the following abbreviations apply:

i=Cl—C(O)—R"/(i-Pr)$_2$NEt, or HO—C(O)—R"/C.A, or [C(O)—R"]2O/(i-Pr)2NEt ii=DMTO-CH2CHO(CEO-P[N(i-Pr)2])-CH2-NHC(O)—R"/Tetr iii=oligonucleotide chain elongation iv=R"—HC=O+[H]

R=5-CPG-Supported P,N-Protected Oligonucleotide

R'=Deprotected NP- or NPS-Oligonucleotide

R"=lipid moiety, L (to which a linker may be conjugated, if desired, see R''' for an example of a conjugated amino glycerol linker)

R'''=—O—CH2(CHOH)CH2-NHC(O)—R"

X=O, S; Y=H, or C(O)—R", Z=O or NH

Figure 3:
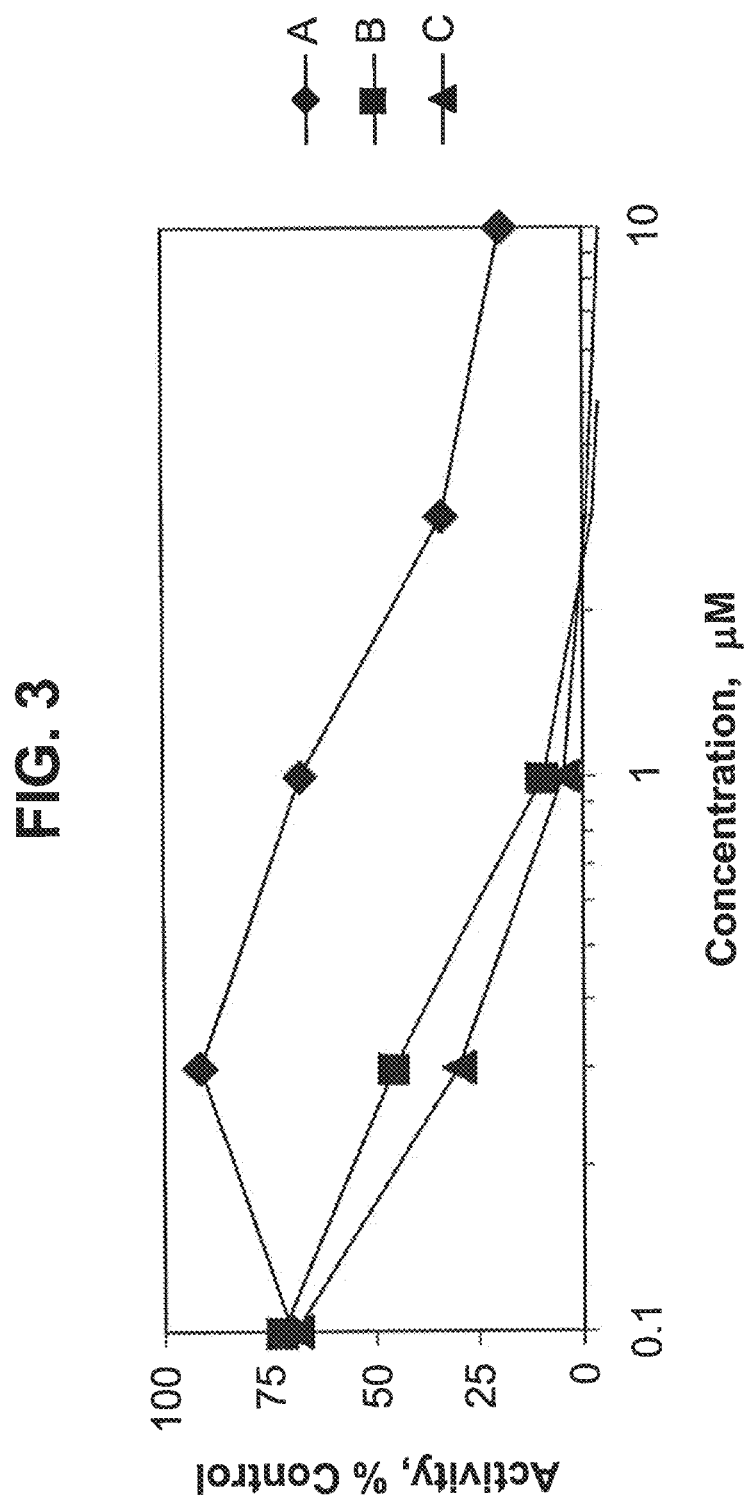
Figure 4:
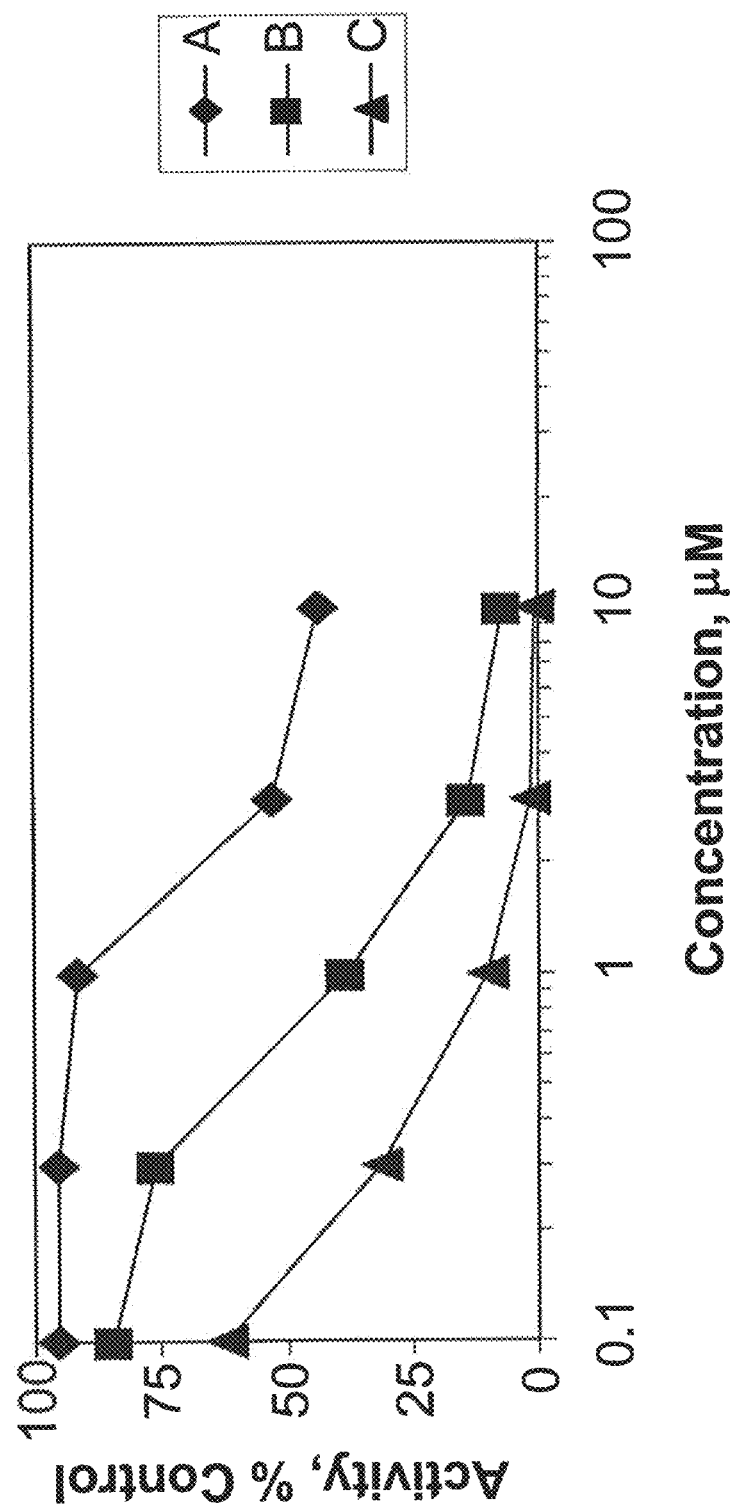

FIGS. 3 and 4 are graphs showing the ability of compounds of the invention to inhibit telomerase activity in U251 and DU145 cells, respectively (see Example 3 for a full description). In these and the following figures, A, B and C are compounds as described in Example 3 and shown in FIG. 9.

Figure 5:
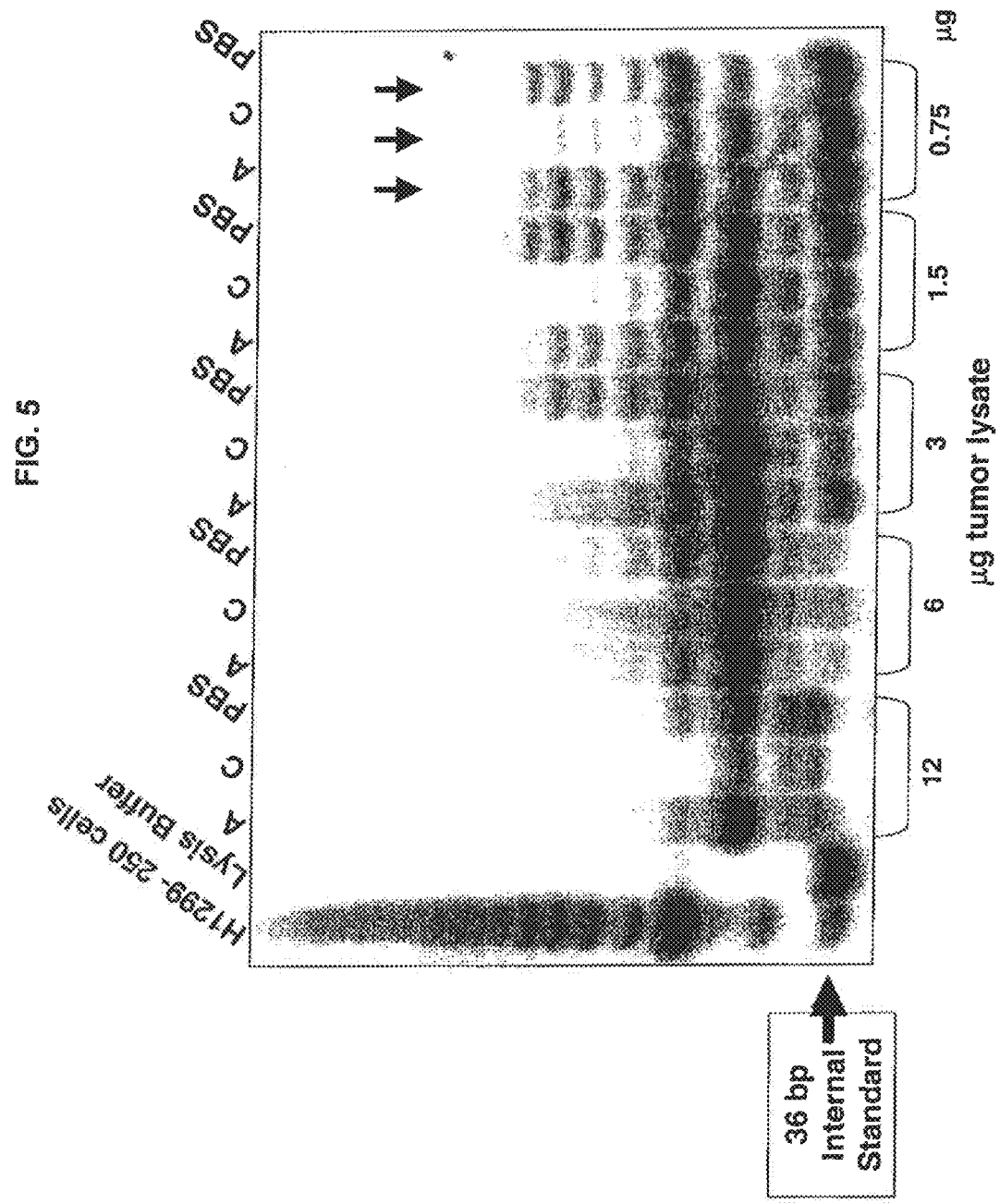

FIG. 5 is an image of a gel showing results of TRAP assays performed on human tumor cells dissected from mice with human tumor xenografts model following treatment with or without compounds of the invention (see Example 4 for a full description).

Figure 6:
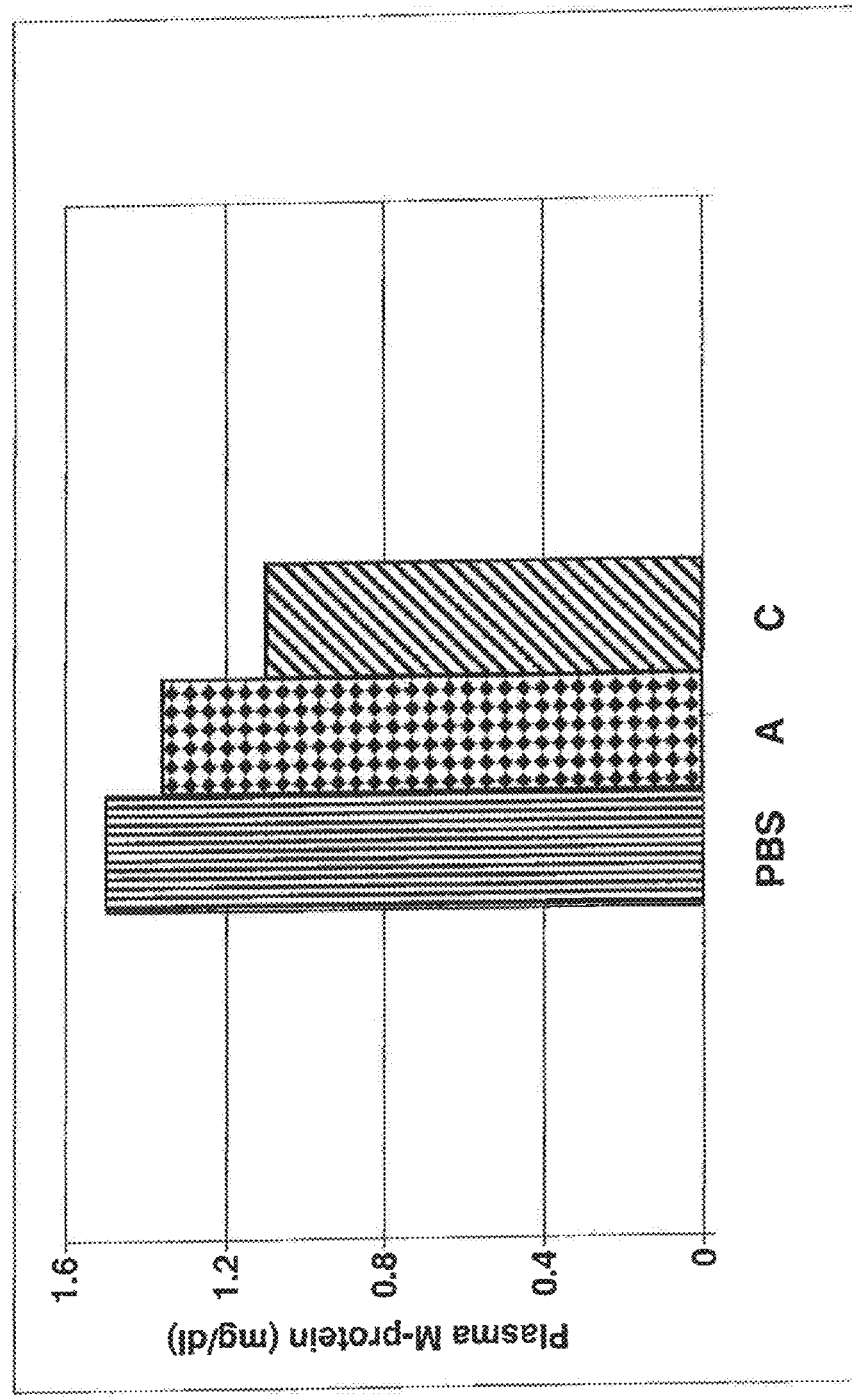

FIG. 6 is a graph showing plasma levels of myeloma protein in mice harboring human myeloma, xenografts following treatment with or without compounds of the invention (see Example 5 for a full description).

Figure 7:
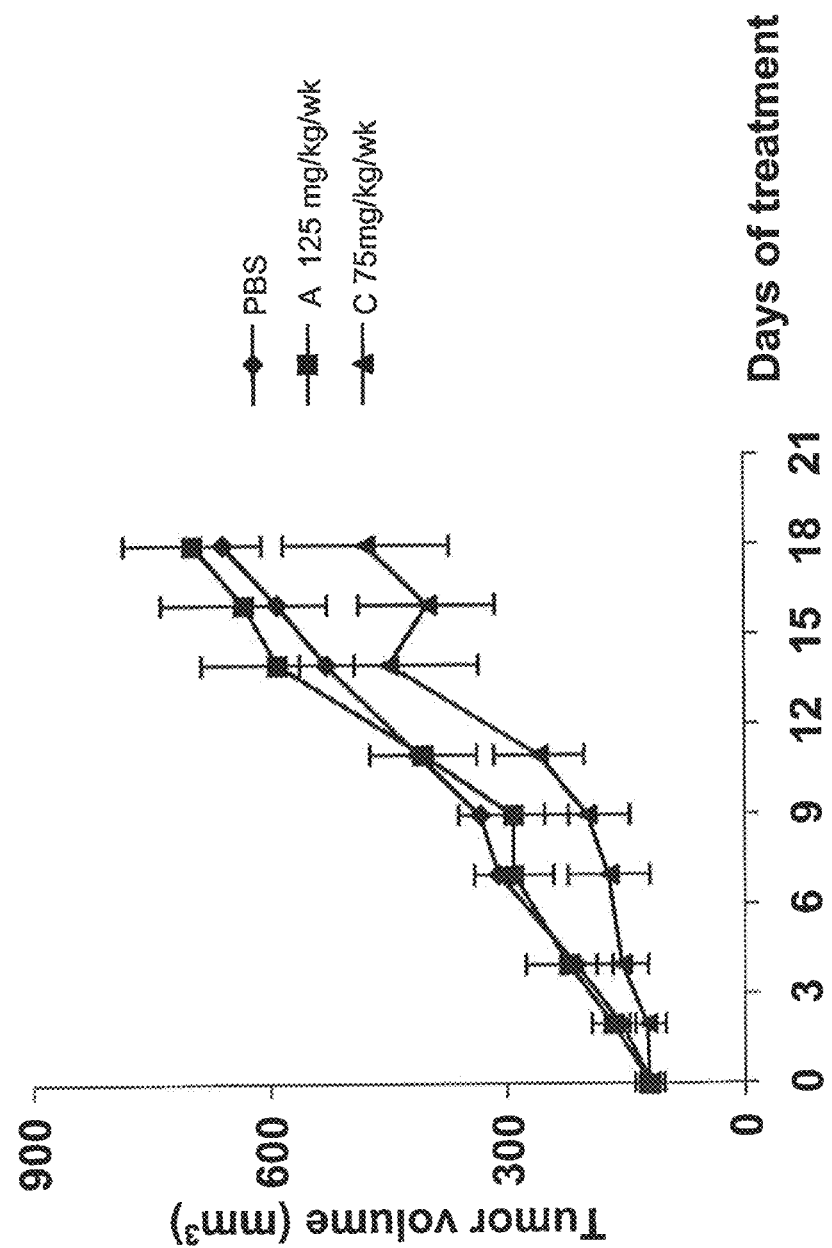
Figure 8:
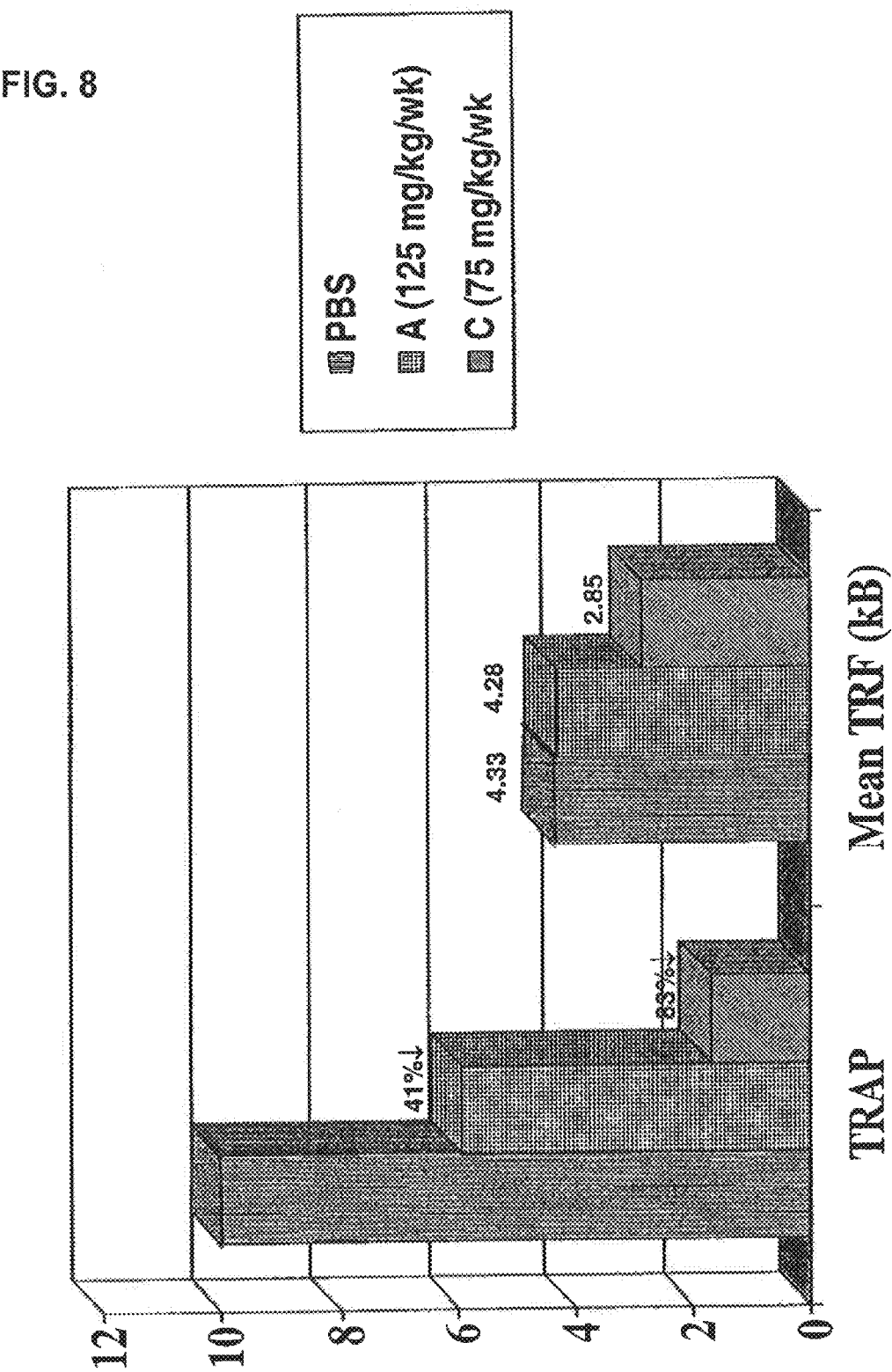

FIGS. 7 and 8 are graphs depicting the effect on tumor volume, telomerase activity and telomere lengths, in mice harboring human myeloma xenografts, with or without administration of compounds of the invention (see Example 6 for a full description).

FIG. 9 depicts the structures of compounds A, B and C utilized in Examples 3-7 in which the oligonucleotide component has thiophosphoramidate linkages.

SEQUENCE LISTING

SEQ ID NO:1 of the accompanying Sequence Listing provides the sequence of the human telomerase RNA component (hTR) (see also Feng et al., Science 269 (5228):1236-1241, 1995, and GenBank, Accession No. U86046). Various oligonucleotides, the sequences of which are complementary to regions contained within SEQ ID NO:1, are referred to throughout this disclosure by reference to the location of the sequence within SEQ ID NO:1 to which they are complementary.

DETAILED DESCRIPTION

A. Definitions

An "alkyl group" refers to an alkyl or substituted alkyl group having 1 to 20 carbon atoms, such as methyl, ethyl, propyl, and the like. Lower alkyl typically refers to $C_1$ to $C_5$. Intermediate alkyl typically refers to $C_6$ to $C_{10}$. An "acyl group" refers to a group having the structure RCO wherein R is an alkyl. A lower acyl is an acyl wherein R is a lower alkyl.

An "alkylamine" group refers to an alkyl group with an attached nitrogen, e.g., 1-methyl1-butylamine ($CH_3CHNH_2CH_2CH_2CH_3$).

An "aryl group" refers to an aromatic ring group having 5-20 carbon atoms, such as phenyl, naphthyl, anthryl, or substituted aryl groups, such as, alkyl- or aryl-substitutions like tolyl, ethylphenyl, biphenylyl, etc. Also included are heterocyclic aromatic ring groups having one or more nitrogen, oxygen, or sulfur atoms in the ring.

"Oligonucleotide" refers to ribose and/or deoxyribose nucleoside subunit polymers having between about 2 and about 200 contiguous subunits. The nucleoside subunits can be joined by a variety of intersubunit linkages, including, but not limited to, phosphodiester, phosphotriester, methylphosphonate, P3'→N5' phosphoramidate, N3'→P5' phosphoramidate, N3'→P5' thiophosphoramidate, and phosphorothioate linkages. Further, "oligonucleotides" includes modifications, known to one skilled in the art, to the sugar (e.g., 2' substitutions), the base (see the definition of "nucleoside" below), and the 3' and 5' termini. In embodiments where the oligonucleotide moiety includes a plurality of intersubunit linkages, each linkage may be formed using the same chemistry or a mixture of linkage chemistries may be used. The term "polynucleotide", as used herein, has the same meaning as "oligonucleotide" and is used interchangeably with "oligonucleotide".

Whenever an oligonucleotide is represented by a sequence of letters, such as "ATGUCCTG," it will be understood that the nucleotides are in 5'→3' order from left to right. Representation of the base sequence of the oligonucleotide in this manner does not imply the use of any particular type of internucleoside subunit in the oligonucleotide.

As used herein, "nucleoside" includes the natural nucleosides, including 2'-deoxy and 2'-hydroxyl forms, e.g., as described in Komberg and Baker, DNA Replication, 2nd Ed. (Freeman, San Francisco, 1992), and analogs. "Analogs" in reference to nucleosides includes synthetic nucleosides having modified nucleobase moieties (see definition of "nucleobase" below) and/or modified sugar moieties, e.g., described generally by Scheit, Nucleotide Analogs (John Wiley, New York, 1980). Such analogs include synthetic nucleosides designed to enhance binding properties, e.g., stability, specificity, or the like, such as disclosed by Uhlmann and Peyman (Chemical Reviews, 90:543-584, 1990).

The term "lipid" is used broadly herein to encompass substances that are soluble in organic solvents, but sparingly soluble, if at all, in water. The term lipid includes, but is not limited to, hydrocarbons, oils, fats (such as fatty acids, glycerides), sterols, steroids and derivative forms of these compounds. Preferred lipids are fatty acids and their derivatives, hydrocarbons and their derivatives, and sterols, such as cholesterol. As used herein, the term lipid also includes amphipathic compounds which contain both lipid and hydrophilic moieties.

Fatty acids usually contain even numbers of carbon atoms in a straight chain (commonly 12-24 carbons) and may be saturated or unsaturated, and can contain, or be modified to contain, a variety of substituent groups. For simplicity, the term "fatty acid" also encompasses fatty acid derivatives, such as fatty amides produced by the synthesis scheme shown in FIG. 2A (see for example, the compounds shown FIGS. 1A-1E).

The term "hydrocarbon" as used herein encompasses compounds that consist only of hydrogen and carbon, joined by covalent bonds. The term encompasses open chain (aliphatic) hydrocarbons, including straight chain and branched hydrocarbons, and saturated as well as mono- and poly-unsaturated hydrocarbons. The term also encompasses hydrocarbons containing one or more aromatic rings.

The term "substituted" refers to a compound which has been modified by the exchange of one atom for another. In particular, the term is used in reference to halogenated hydrocarbons and fatty acids, particularly those in which one or more hydrogen atoms are substituted with fluorine.

A "nucleobase" as used herein includes (i) typical DNA and RNA nucleobases (uracil, thymine, adenine, guanine, and cytosine), (ii) modified nucleobases or nucleobase analogs (e.g., 5-methyl-cytosine, 5-bromouracil, or inosine) and (iii) nucleobase analogs. A nucleobase analog is a chemical whose molecular structure mimics that of a typical DNA or RNA base.

As used herein, "pyrimidine" means the pyrimidines occurring in natural nucleosides, including cytosine, thymine, and uracil, and analogs thereof, such as those containing oxy, methyl, propynyl, methoxy, hydroxyl, amino, thio, halo, and substituents. The term as used herein further includes pyrimidines with protection groups attached, such as $N_4$-benzoylcytosine. Further pyrimidine protection groups are disclosed by Beaucage and Iyer (Tetrahedron 48:223-2311, 1992).

As used herein, "purine" means the purines occurring in natural nucleosides, including adenine, guanine, and hypoxanthine, and analogs thereof, such as those containing oxy, methyl, propynyl, methoxy, hydroxyl, amino, thio, halo, and substituents. The term as used herein further includes purines with protection groups attached, such as $N_2$-benzoylguanine, $N_2$-isobutyrylguanine, $N_6$-benzoyladenine, and the like. Further purine protection groups are disclosed by Beaucage and Iyer (cited above).

As used herein, the term "protected" as a component of a chemical name refers to art-recognized protection groups for a particular moiety of a compound, e.g., "5'-protected-hydroxyl" in reference to a nucleoside includes triphenylmethyl (i.e., trityl), p-anisyldiphenylmethyl (i.e., monomethoxytrityl or MMT), di-p-anisylphenylmethyl (i.e., dimethoxytrityl or DMT), and the like. Art-recognized protection groups include those described in the following references: Gait, editor, Oligonucleotide Synthesis: A Practical Approach (IRL Press, Oxford, 1984); Amarnath and Broom, Chemical Reviews, 77:183-217, 1977; Pon et al., Biotechniques, 6:768-775, 1988; Ohtsuka at al., Nucleic Acids Research, 10:6553-6570, 1982; Eckstein, editor, Oligonucleotides and Analogues: A Practical Approach (IRL Press, Oxford, 1991); Greene and Wuts, Protective Groups in Organic Synthesis, Second Edition, (John Wiley & Sons, New York, 1991); Narang, editor, Synthesis and Applications of DNA and RNA (Academic Press, New York, 1987); Beaucage and Iyer (cited above), and like references.

The term "halogen" or "halo" is used in its conventional sense to refer to a chloro, bromo, fluoro or iodo substituent. In the compounds described and claimed herein, halogen substituents are generally fluoro, bromo, or chloro, preferably fluoro or chloro.

B. Design of Invention Compounds

The compounds of the invention may be represented by the formula:

$$O\text{-}(x\text{-}L)_n,$$

where O represents the oligonucleotide, x is an optional linker group, L represents the lipid moiety and n is an integer from 1-5.

Design of the compounds therefore requires the selection of two entities, O and L, and the determination of the structural linkage(s) between these entities, which may involve the optional linker group x.

Selection of O

The oligonucleotide component O may be regarded as the "effector" component of the compound in that it is this component that effects inhibition of the telomerase enzyme by binding to the RNA component of telomerase. Thus, the sequence of O is selected such that it includes a region that is complementary to the sequence of the telomerase RNA, which is shown in SEQ ID NO:1. The region that is complementary to the telomerase RNA component may in theory be targeted to any portion of the telomerase RNA, but particular regions of the telomerase RNA are preferred target for inhibitory oligonucleotides. One preferred target region is the region spanning nucleotides 30-67 of SEQ ID NO:1, which includes the "template region," an 11 nucleotide region of sequence 5'-CUAACCCUAAC-3' that spans nucleotide 46-56 of SEQ ID NO: 1. The template region functions to specify the sequence of the telomeric repeats that telomerase adds to the chromosome ends and is essential to the activity of the telomerase enzyme (see Chen at al., Cell 100:503-514, 2000; Kim et al., Proc. Natl. Acad. Sci., USA 98 (14):7982-7987, 2001). Compounds of the invention that contain an oligonucleotide moiety comprising a sequence complementary to all or part of the template region are thus particularly preferred. Another preferred target region is the region spanning nucleotides 137-179 of hTR (see Pruzan et al, Nucl. Acids Research, 30:559-588, 2002). Within this region, the sequence spanning 141-153 is a preferred target. PCT publication WO 98/28442 describes the use of oligonucleotides of at least 7 nucleotides in length to inhibit telomerase, where the oligonucleotides are designed to be complementary to accessible portions of the hTR sequence outside of the template region, including nucleotides 137-196, 290-319, and 350-380 of hTR.

The region of O that is targeted to the hTR sequence is preferably exactly complementary to the corresponding hTR sequence. While mismatches may be tolerated in certain instances, they are expected to decrease the specificity and activity of the resultant oligonucleotide conjugate. In particular embodiments, the base sequence of the oligonucleotide O is thus selected to include a sequence of at least 5 nucleotides exactly complementary to the telomerase RNA, and enhanced telomerase inhibition may be obtained if increasing lengths of complementary sequence are employed, such as at least 8, at least 10, at least 12, at least 13 or at least 15 nucleotides exactly complementary to the telomerase RNA. In other embodiments, the sequence of the oligonucleotide includes a sequence of from at least 5 to 20, from at least 8 to 20, from at least 10 to 20 or from at least 10 to 15 nucleotides exactly complementary to the telomerase RNA sequence. Optimal telomerase inhibitory activity may be obtained when the full length of the oligonucleotide O is selected to be complementary to the telomerase RNA. However, it is not necessary that the full length of the oligonucleotide component be exactly complementary to the target sequence, and the oligonucleotide sequence may include regions that are not complementary to the target sequence. Such regions may be added, for example, to confer other properties on the compound, such as sequences that facilitate purification. If the oligonucleotide component O is to include regions that are not complementary to the target sequence, such regions are typically positioned at one or both of the 5' or 3' termini. In instances where the region of exact complementarity is targeted to the template region, effective telomerase inhibition may be achieved with a short (5-8 nucleotide) region of exact complementarity to which a telomerase-like (G-rich) sequence is joined at the 5' end.

Exemplary sequences that are complementary to the human telomerase RNA and which may be included as part of the oligonucleotide component O, or which may be used as the entire oligonucleotide component O include the following:

| Oligonucleotide sequence | hTR complementary sequence (region of SEQ ID NO: 1) |
|---|---|
| GCTCTAGAATGAACGGTGGAAGGCGGCAGG | 137-166 |
| GTGGAAGGCGGCAGG | 137-151 |
| GGAAGGCGGCAGG | 137-149 |
| GTGGAAGGCGGCA | 139-151 |
| GTGGAAGGCGG | 141-151 |
| CGGTGGAAGGCGG | 141-153 |
| ACGGTGGAAGGCG | 142-154 |
| AACGGTGGAAGGCGGC | 143-155 |
| ATGAACGGTGGAAGGCGG | 144-158 |
| ACATTTTTGTTTGCTCTAG | 160-179 |
| TAGGGTTAGACAA | 42-54 |
| GTTAGGGTTAG | 46-56 |
| GTTAGGGTTAGAC | 44-56 |
| GTTAGGGTTAGACAA | 42-56 |
| GGGTTAGAC | 44-52 |
| CAGTTAGGG | 50-58 |
| CCCTTCTCAGTT | 54-65 |
| CGCCCTTCTCAG | 56-67 |

The choice of the type of inter-nucleoside linkages used in the synthesis of the O component may be made from any of the available oligonucleotide chemistries, including but not limited to, phosphodiester, phosphotriester, methylphosphonate, P3'→N5' phosphoramidate, N3'→P5' phosphoramidate, N3'→P5' thiophosphoramidate, and phosphorothioate linkages.

In preferred embodiments, the oligonucleotide component O has at least one N3'→P5' phosphoramidate or N3'→P5' thiophosphoramidate linkage, which linkage may be represented by the structure:

3'-[-NH—P(=O)(—XR)—O-]-5', wherein X is O or S and R is selected from the group consisting of hydrogen, alkyl, and aryl; and pharmaceutically acceptable salts thereof.

Typically, but not necessarily, all of the internucleoside linkages within the oligonucleotide O will be of the same type, although the oligonucleotide component may be synthesized using a mixture of different linkages. Where the lipid moiety is to be conjugated to the 3' terminus of the oligonucleotide, the synthesis of the conjugate is greatly facilitated by a 3' amino group on the oligonucleotide. Hence, even if one of the preferred chemistries is not selected, the addition of a 3' amino group is advantageous.

Selection of L

The compounds of the invention are more effective in producing telomerase inhibition in cells than corresponding oligonucleotides that are not conjugated to lipid components. The lipid component L is believed to function to enhance cellular uptake of the compound, particularly in facilitating passage through the cellular membrane. While the mechanism by which this occurs has not been fully elucidated, one possibility is that the lipid component may facilitate binding of the compound to the cell membrane as either a single molecule, or an aggregate (micellar) form, with subsequent internalization. However, understanding of the precise mechanism is not required for the invention to be utilized.

The lipid component may be any lipid or lipid derivative that provides enhanced cellular uptake compared to the unmodified oligonucleotide. Preferred lipids are hydrocarbons, fats (e.g., glycerides, fatty acids and fatty acid derivatives, such as fatty amides) and sterols. Where the lipid component is a hydrocarbons, the L component may be a substituted or unsubstituted cyclic hydrocarbon or an aliphatic straight chain or branched hydrocarbon, which may be saturated or unsaturated. Preferred examples are straight chain unbranched hydrocarbons that are fully saturated or polyunsaturated. The length of the hydrocarbon chain may vary from $C_2$-$C_{30}$, but optimal telomerase inhibition may be obtained with carbon chains that are $C_8$-$C_{22}$. Preferred examples of saturated hydrocarbons (alkanes) are listed below:

| Systematic name | Carbon chain |
| --- | --- |
| Tetradecane | $C_{14}H_{30}$ |
| Pentadecane | $C_{15}H_{32}$ |
| Hexadecane | $C_{16}H_{34}$ |
| Heptadecane | $C_{17}H_{36}$ |
| Octadecane | $C_{18}H_{38}$ |
| Nonadecane | $C_{19}H_{40}$ |
| Eicosane | $C_{20}H_{42}$ |

Mono- and poly-unsaturated forms (alkenes and polyenes, such as alkadienes and alkatrienes) of hydrocarbons may also be selected, with compounds having one to three double bonds being preferred, although compound having more double bonds may be employed. Alkynes (containing one or more triple bonds) and alkenynes (triple bond(s) and double bond(s)) may also b utilized. Examples of common mono- and poly-unsaturated hydrocarbons that may be employed include those shown in FIGS. 1M, 1L and 1O.

Substituted forms of hydrocarbons may be employed in the compounds of the invention, with substituent groups that are inert in vivo and in vitro being preferred. A particularly preferred substituent is fluorine. Exemplary generic structures of polyfluorinated hydrocarbons include:

$CF_3(CF_2)_n$—$(CH_2)_m$— where m is at least 1, preferably at least 2, and n=1-30, such as fluorotridecane: $CF_3(CF_2)_9(CH_2)_3$; and $CH_3(CH_2)_a(CF_2)_b(CH_2)_c$— where a, b and c are independently 1-30.

Figure 1E:
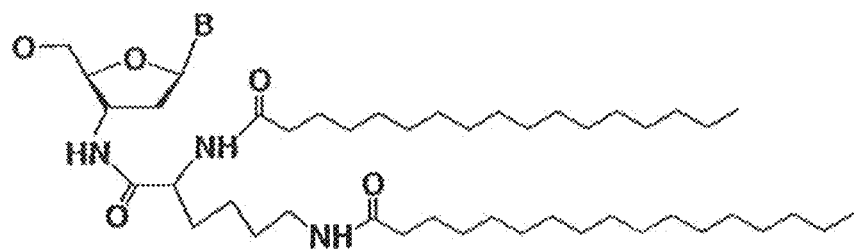
FIG. 1 shows examples of the attachment of various lipid L groups to oligonucleotides in compounds of the invention.
Figure 1F:
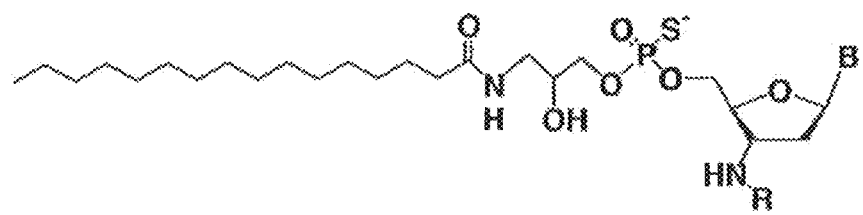
Figure 1G:
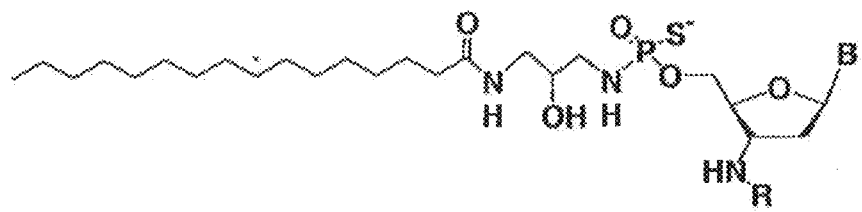
Figure 1H:
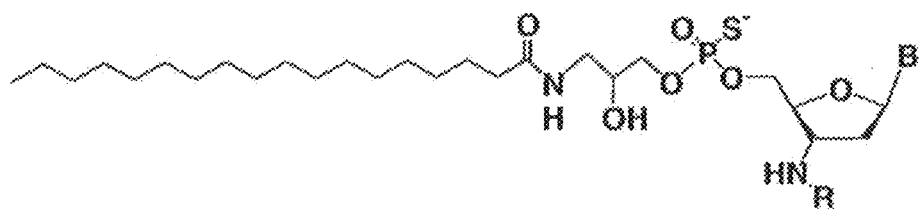
Figure 1I:
Figure 1J:
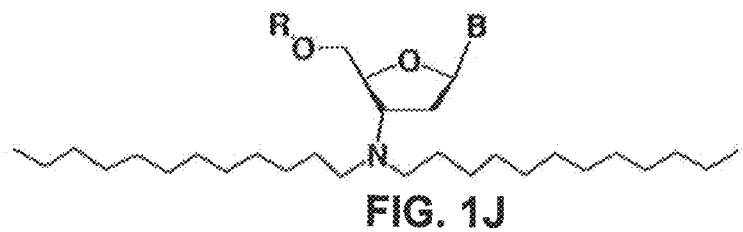
Figure 1K:
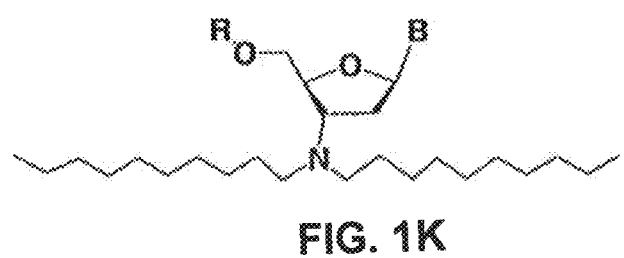
Figure 1L:
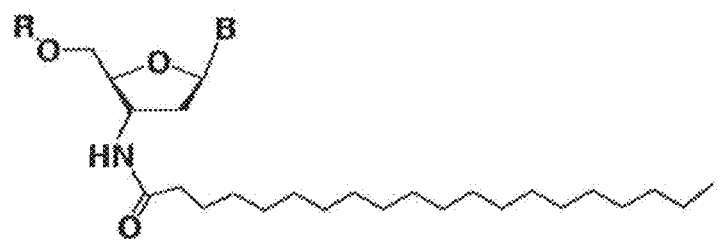
Figure 1M:
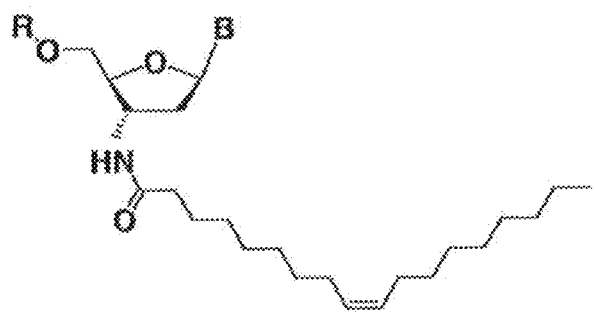
Figure 1N:
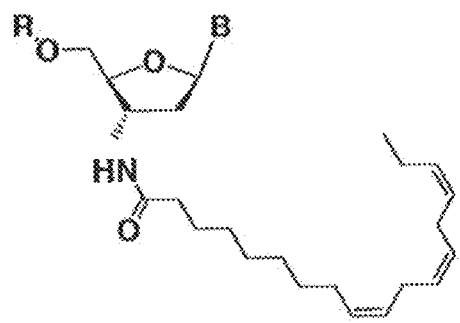
Figure 1O:
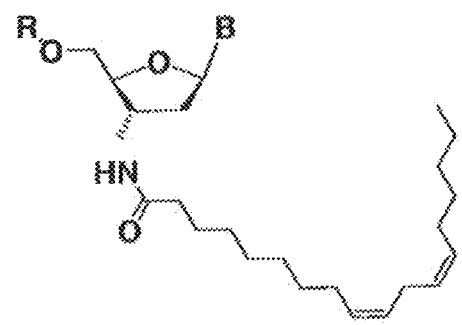
Figure 1P:
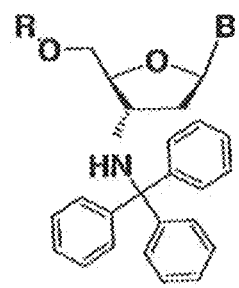
Figure 1Q:
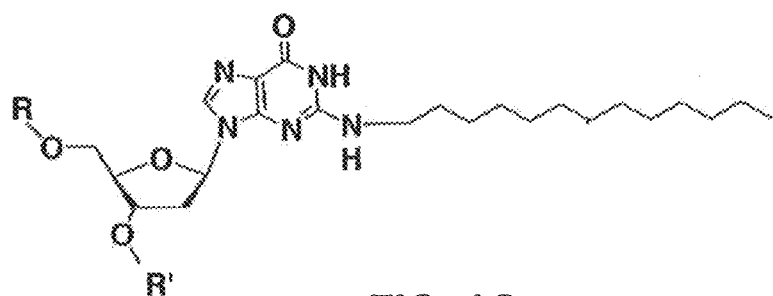
Figure 1R:
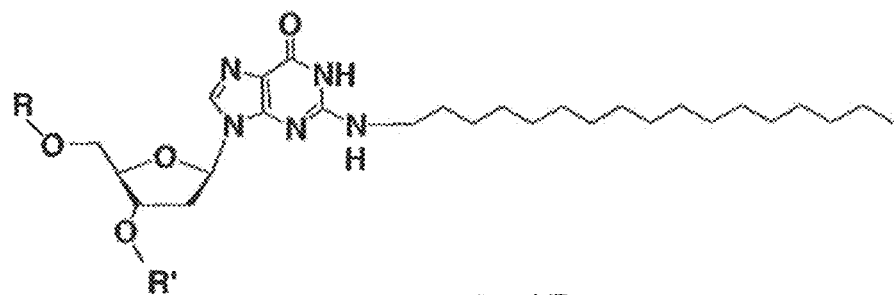
Figure 1S:
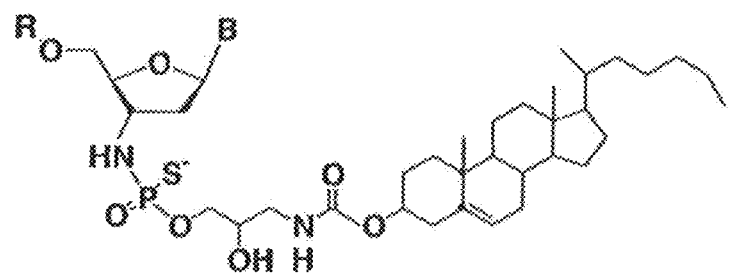
Figure 1T:
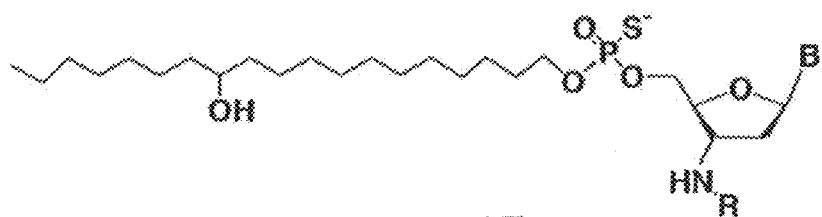
Figure 1U:
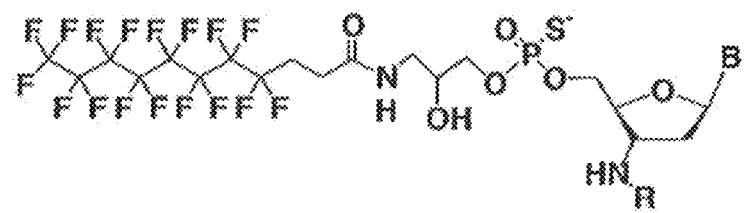
Figure 1V:
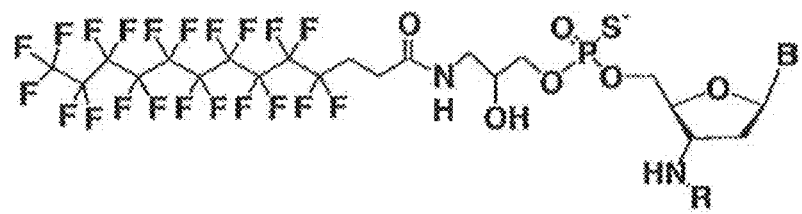
Figure 1W:
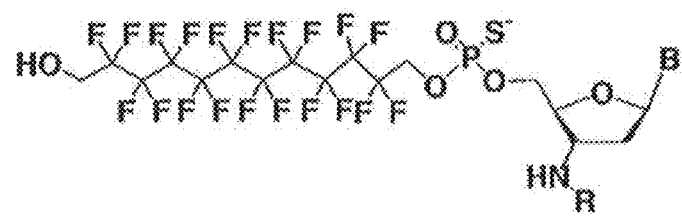
Figure 1X:
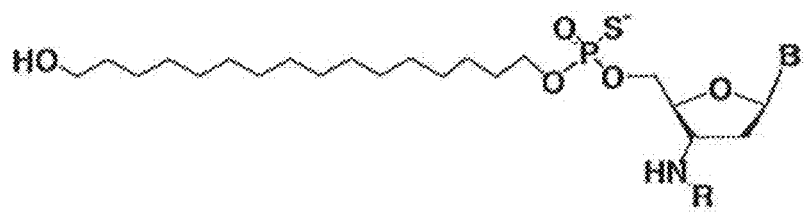
Figure 1Y:
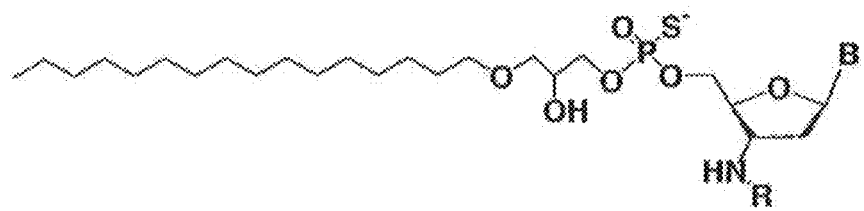

FIG. 1W shows an example of a polyfluorinated hydrocarbon conjugated to the 5' terminus of an oligonucleotide.

Other suitable lipid components include simple fatty acids and fatty acid derivatives, glycerides and more complex lipids such as sterols, for example cholesterol. Fatty acids and their derivatives may be fully saturated or mono- or poly-unsaturated. The length of the carbon chain may vary from $C_2$-$C_{30}$, but optimal telomerase inhibition may be obtained with carbon chains that are $C_8$-$C_{22}$. Preferred examples of saturated fatty acids are listed below:

| Systematic name | Trivial name | Carbon chain |
| --- | --- | --- |
| Tetradecanoic | myristic | 14:0 |
| Hexadecanoic | palmitic | 16:0 |
| Octadecanoic | stearic | 18:0 |
| Eicosanoic | arachidic | 20:0 |

Mono- and poly-unsaturated forms of fatty acids may also be employed, with compounds having one to three double bonds being preferred, although compounds having more double bonds may also be employed. Examples of common mono- and poly-unsaturated fatty acids that may be employed include:

| Systematic name | Trivial name | Carbon chain |
| --- | --- | --- |
| Cis-9-hexadecanoic | palmitoleic | 16:1 (n-7) |
| Cis-6-octadecanoic | petroselinic | 18:1 (n-12) |
| Cis-9-octadecanoic | oleic | 18:1 (n-9) |
| 9,12-octadecadienoic | linoleic | 18:2 (n-6) |
| 6,9,12-octadecatrienoic | gamma-linolenic | 18:3 (n-6) |
| 9,12,15-octadecatrienoic | alpha-linolenic | 18:3 (n-3) |
| 5,8,11,14-eicosatetraenoic | arachidonic | 20:4 (n-6) |

Fatty acids with one or more triple bonds in the carbon chain, as well as branched fatty acids may also be employed in the compounds of the invention. Substituted forms of fatty acids may be employed in the compounds of the invention. As with the hydrocarbon groups, substituent groups that are inert in vivo and in vitro are preferred, with fluorine being a particularly preferred. Exemplary generic structures of polyfluorinated derivatives of fatty acids suitable for use in the invention are:

$CF_3(CF_2)_n$—$(CH_2)_m CO$— where m is at least 1, preferably at least 2, and n=1-30, and $CH_3(CH_2)_a(CF_2)_b(CH_2)_c CO$— where a, b and c are independently 1-30

Examples of compounds of the invention having polyfluorinated derivatives of fatty acids are shown in FIGS. 1U and 1V.

Typically between one and five L components (n=1-5) are covalently linked to the O component, optionally via a linker. More usually 1 or two L components are utilized (n=1 or 2). Where more than one L component is linked to the O component, each L component is independently selected.

It will be appreciated that compounds of the invention described as having a specified hydrocarbon as the L moiety and compounds described as having a specified fatty acid (with the same number of carbon atoms as the specified hydrocarbon) are closely related and differ in structure only in the nature of the bond that joins the L moiety to the oligonucleotide, which in turn is a result of the synthesis procedure used to produce the compound. For example, and as described in more detail below, when compounds are synthesized having the L moiety conjugated to the 3'-amino terminus of an oligonucleotide (having phosphoramidate or thiophosphoramidate internucleoside linkages), the use of the aldehyde form of a fatty acid (a fatty aldehyde) as the starting material results in the formation of an amine linkage between the lipid chain and the oligonucleotide, such that the lipid group appears as a hydrocarbon. In contrast, use of the carboxylic acid, acid anhydride or acid chloride forms of the same fatty acid results in the formation of an amide linkage, such that the lipid group appears as a fatty acid derivative, specifically in this instance a fatty amide (as noted in the definitions section above, for the sake of simplicity, the term "fatty acid" when describing the conjugated L group is used broadly herein to include fatty acid derivatives, including fatty amides). This is illustrated in the following schematics (and in FIGS. 2A and 2C) which depict the 3'-amino terminus of a phosphoramidate oligonucleotide joined to a $C_{14}$ lipid component. In schematic A, L is tetradecanoic acid (myristic acid), in which the connection between L and O groups is an amide. In schematic B, L is tetradecane, and the connection between the L and O groups is an amine.

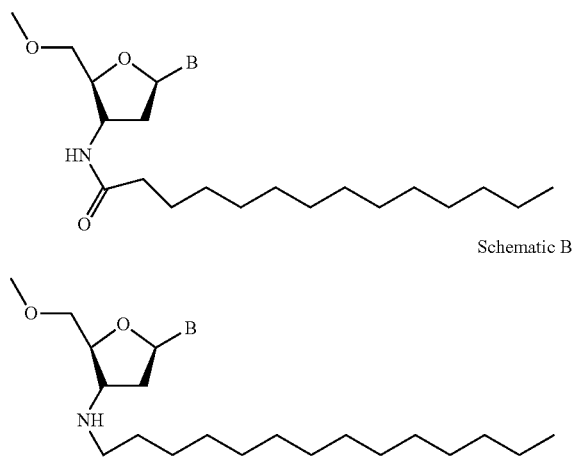

Schematic A

Schematic B

Linkage of O and L Components

The linkage between the O and L components may be a direct linkage, or may be via an optional linker moiety, x. The linker group may serve to facilitate the chemical synthesis of the compounds (discussed in the synthesis section below). Whether or not a linker group is used to mediate the conjugation of the O and L components, there are multiple sites on the oligonucleotide component O to which the L component(s) may be conveniently conjugated. Suitable linkage points include the 5' and 3' termini, one or more sugar rings, the internucleoside backbone and the nucleobases of the oligonucleotide. Typically, the L moiety is attached to the 3' or 5' terminus of the oligonucleotide.

Figure 1Z:
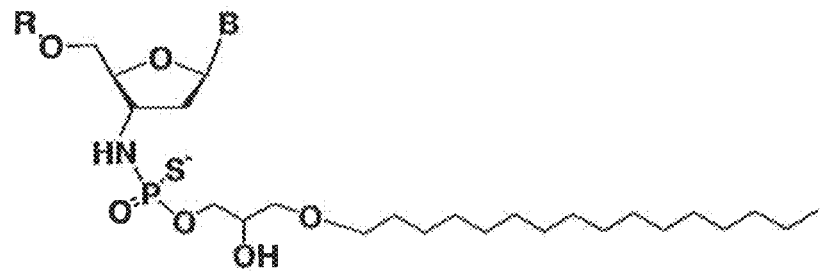
Figure 1A:
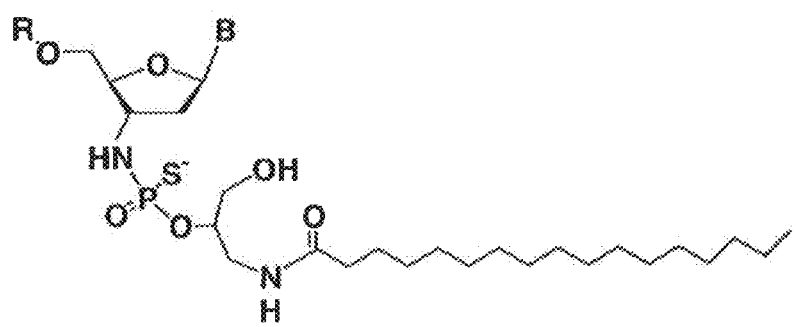
Figure 1B:
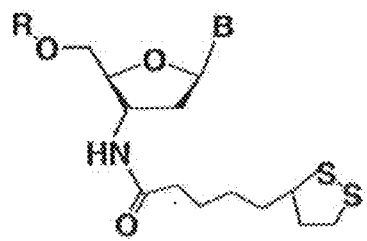
Figure 1C:
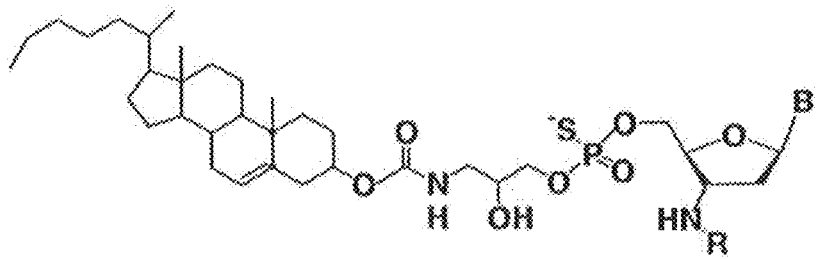

If the L component is to be attached to the 3' terminus, the attachment may be directly to the 3' substituent, which in the case of the preferred phosphoramidate and thiophosphoramidate oligonucleotides is the 3'-amino group (examples are shown in FIGS. 1A-C), and in other instances, such as conventional phosphodiester oligonucleotides, is a 3-hydroxy group. Alternatively, the L moiety may be linked via a 3'-linked phosphate group (an example is shown in FIG. 1Z, in which a hexadecane hydrocarbon is linked to the 3' phosphate of a thiophosphoramidate oligonucleotide through an O-alkyl linker. If the L moiety is to be linked to the 5' terminus, it is typically attached through a 5'-linked phosphate group (see FIG. 1F which shows the use of an amino glycerol linker, and FIG. 1G which shows the use of a bis-amino glycerol linker). Attachment to a base on the O moiety may through any suitable atom, for example to the $N^2$ amino group of guanosine (see FIGS. 1Q-R). Where n>1 such that a plurality of lipid moieties is to be attached to the O component, the individually selected L components may be attached at any suitable site(s). For example, one L group may be attached to each terminus, various L groups may be attached to the bases, or two or more L groups may be attached at one terminus (see FIGS. 1E, 1J, 1K).

The optional linker component x may be used to join the O and L components of the compounds. If a linker is to be employed, it is incorporated into the synthesis procedures as described in the legend to FIG. 2, above. Examples of suitable linker groups include amino glycerol and O-alkyl glycerol-type linkers which respectively can be depicted by the generic structures:

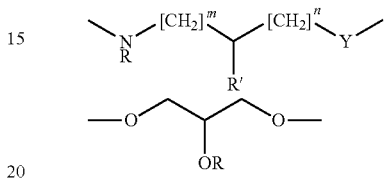

Wherein R'=H, OH, $NH_2$ or SH; Y=O, S or NR; R=H or alkyl; and n and m are independently integers between 1-18.

Specific examples of suitable linkers are the aminoglycerol linker in which R'=OH, Y=O, and m and n are each 1:

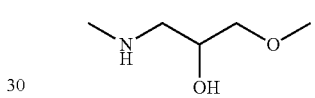

the bis-aminoglycerol linker, in which R'=OH, Y=NH, and m and n are each 1:

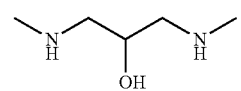

and the O-alkyl glycerol linker in which R=H:

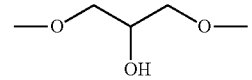

C. Examples of Invention Compounds

Figure 1D:
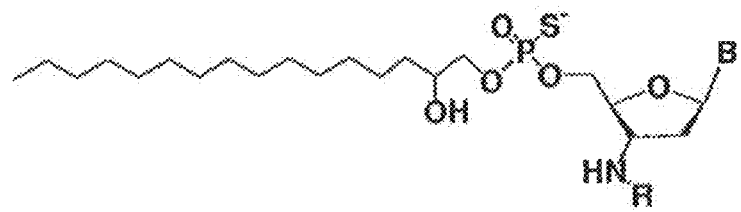

Examples of invention compounds are shown in FIG. 1. For simplicity, only one base of the oligonucleotide O is shown, with a generic base, B, being depicted and R indicating the attachment point for the remainder of the oligonucleotide. Compounds linked to the 3' terminus are illustrated with a 3'-nitrogen, consistent with the preferred thiophosphoramidate and phosphoramidate oligonucleotide chemistries. FIGS. 1A-1L illustrate compounds having saturated lipid groups attached to the 5' or 3' termini. FIGS. 1M-1P illustrate compounds having mono- or poly-unsaturated lipid groups. FIGS. 1Q-1R illustrate compounds having lipid groups conjugated to the oligonucleotide through a base (in this case, guanosine). FIGS. 1S and 1CC illustrate 3'- and 5'-conjugated cholesterol lipid moiety, respectively. FIGS. 1U and 1V illustrate 5'-conjugated polyfluorine substituted fatty acid derivatives, and FIG. 1W illustrates a 5' conjugated polyfluorinated hydrocarbon. FIGS. 1X-Z illustrate 5' lipid moieties containing oxygen. The nomenclatures used herein for each of the lipid groups illustrated are as follows:

FIG. 1A: 3'-myristoylamide
FIG. 1B: 3'-palmitoylamide
FIG. 1C: 3'-stearoylamide
FIG. 1D: 3'-palmitoylamido-propyl-thiophosphate
FIG. 1E: 3'-lysyl-bis-stearoylamide
FIG. 1F: 5'-palmitoylamido-aminoglycerol-thiophosphate
FIG. 1G: 5'-palmitoylamido-bis-aminoglycerol-thiophosphate
FIG. 1H: 5'-stearoylamido-aminoglycerol-thiophosphate
FIG. 1I: 3'-dodecyl
FIG. 1J: 3'-bis-dodecyl
FIG. 1K: 3' bis-decyl
FIG. 1L: 3'-eicosanoylamide
FIG. 1M: 3'-oleinylamide
FIG. 1N: 3'-linolenylamide
FIG. 1O: 3'-linoleylamide
FIG. 1P: 3'-trityl
FIG. 1Q: $N^2$-tetradecyl guanosine
FIG. 1R: $N^2$-octadecyl-guanosine
FIG. 1S: 3'-cholesterylamido-aminoglycerol-thiophosphate
FIG. 1T: 5'-(12-OH)-stearoyl-thiophosphate
FIG. 1U: 5'-C11-teflon-thiophosphate
FIG. 1V: 5'-C13-teflon-thiophosphate
FIG. 1W: 5'—OH—C10-Teflon-thiophosphate
FIG. 1X: 5'-OH-palmityl-thiophosphate
FIG. 1Y: 5'-batyl-thiophosphate
FIG. 1Z: 3'-batyl-thiophosphate
FIG. 1AA: 3'-palmitoylamido-aminoglycerol-thiophosphate
FIG. 1BB: 3'-thioctylamide
FIG. 1CC: 5'-cholesterylamido-aminoglycerol-thiophosphate
FIG. 1DD: 5'-(2-OH)-hexadecanol-thophosphate D. Synthesis of the Invention Compounds The oligonucleotide components of the invention compounds may be synthesized using standard protocols for the type of chemistry selected. Methods for the synthesis of oligonucleotides having the preferred N3'→P5' phosphoramidate and N3'→P5' thiophosphoramidate chemistries are described in McCurdy et al., (1997) Tetrahedron Letters, 38:207-210 and Pongracz & Gryaznov, (1999) Tetrahedron Letters, 49:7661-7664, respectively.

A variety of synthetic approaches can be used to conjugate the lipid moiety L to the oligonucleotide, depending on the nature of the linkage selected, including the approaches described in Mishra et al., (1995) Biochemica et Biophysica Acta, 1264:229-237, Shea et al., (1990) Nucleic Acids Res. 18:3777-3783, and Rump et al., (1998) Bioconj. Chem. 9:341-349. The synthesis of compounds of the invention in which the lipid moiety is conjugated at the 5' or 3' terminus of the oligonucleotide can be achieved through use of suitable functional groups at the appropriate terminus, most typically an amino group, which can be reacted with carboxylic acids, acid chlorides, anhydrides and active esters. Thiol groups are also suitable as functional groups (see Kupihar et al., (2001) Bioorganic and Medicinal Chemistry 9:1241-1247). Both amino- and thiol-modifiers of different chain lengths are commercially available for oligonucleotide synthesis. Oligonucleotides having N3'→P5' phosphoramidate and N3'→P5' thiophosphoramidate linkages contain 3'-amine groups (rather than 3'-hydroxy found in most conventional oligonucleotide chemistries), and hence these oligonucleotides provide a unique opportunity for conjugating lipid groups to the 3'-end of the oligonucleotide.

Figure 2D:
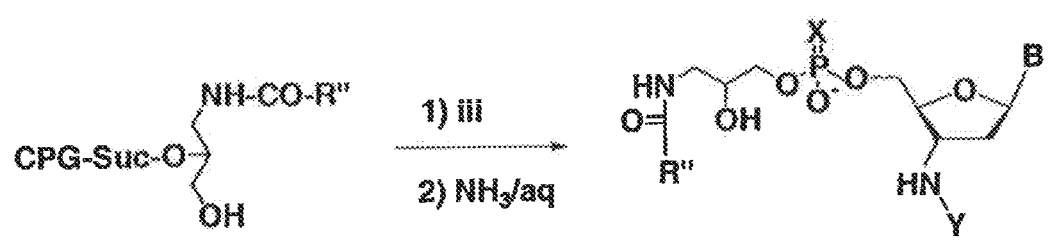
FIG. 2D shows a synthesis procedure that may be used for the production of compounds in which the lipid moiety is conjugated to the 5' terminus of the oligonucleotide through a phosphate group (or thiophosphate when X=S). In these schematics, the 3' terminus of the oligonucleotide is shown as an amino group, consistent with the preferred oligonucleotide linkages of thiophosphoramidate (X=S) and phosphoramidate (X=O) chemistries.

Various approaches can be used to attach lipid groups to the termini of oligonucleotides with the preferred N3'→P5' phosphoramidate and N3'→P5' thiophosphoramidate chemistries. Examples of synthetic schemes for producing the conjugated compounds of the invention are shown in FIG. 2. For attachment to the 3' terminus, the conjugated compounds can be synthesized by reacting the free 3'-amino group of the fully protected solid support bound oligonucleotide with the corresponding acid anhydride followed by deprotection with ammonia and purification. Alternatively, coupling of carboxylic acids of lipids to the free 3'-amino group of the support bound oligonucleotide using coupling agents such as carbodiimides, HBTU or 2-chloro-1-methylpyridinium iodide can be used to conjugate the lipid groups. These two methods will form an amide bond between the lipid and the oligonucleotide. Lipids may also be attached to the oligonucleotide chain using a phosphoramidite derivative of the lipid coupled to the oligonucleotides during chain elongation. This approach yields a phosphoramidate or thiophosphoramidate linkage connecting the lipid and the oligonucleotide (exemplified by propyl-palmitoyl and 2-hydroxy-propyl-palmitoyl compounds). Still another approach involves reaction of the free 3'-amino group of the fully protected support bound oligonucleotide with a suitable lipid aldehyde, followed by reduction with sodium cyanoborohydride, which produces an amine linkage.

For attachment to the 5' terminus, the oligonucleotide can be synthesized using a modified, lipid-containing solid support, followed by synthesis of the oligonucleotide in the 5- to 3' direction as described in Pongracz & Gryaznov (1999). An example of the modified support is provided in Schematic C below. In the instance where n=14, the fatty acid is palmitic acid: reaction of 3-amino-1,2-propanediol with palmitoyl chloride, followed by dimethoxytritylation and succinylation provided the intermediate used for coupling to the solid support. R is long chain alkyl amine controlled pore glass.

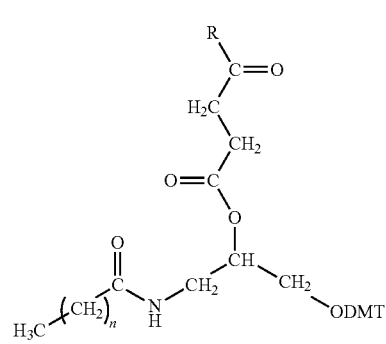

Schematic C

E. Telomerase Inhibition Assays

The conjugates of the present invention may be used to inhibit or reduce telomerase enzyme activity and/or proliferation of cells having telomerase activity. In these contexts, inhibition or reduction of the enzyme activity or cell proliferation refer to a lower level of the measured activity relative to a control experiment in which the enzyme or cells are not treated with the conjugate. In particular embodiments, the inhibition or reduction in the measured activity is at least a 10% reduction or inhibition. One of skill in the art will appreciate that reduction or inhibition of the measured activity of at least 20%, 50%, 75%, 90% or 100% may be preferred for particular applications. The ability of the invention compounds to inhibit telomerase can be determined in a cell-free assay (referred to as a biochemical assay) and in cells.

Methods for measuring telomerase activity, and the use of such methods to determine the telomerase inhibitory activity of compounds are well known. For example, the TRAP assay is a standard assay method for measuring telomerase activity in a cell extract system and has been widely used in the search for telomerase inhibiting compounds (Kim et al., Science 266:2011, 1997; Weinrich et al., Nature Genetics 17:498, 1997). The TRAP assay measures the amount of radioactive nucleotides incorporated into elongation products (polynucleotides) formed by nucleotide addition to a telomerase substrate or primer. The radioactivity incorporated can be measured as the intensity of a band on a detection screen (e.g., a Phosphorimager screen) exposed to a gel on which the radioactive products are separated. The TRAP assay is also described in detail in U.S. Pat. Nos. 5,629,154, 5,837,453 and 5,863,726, and its use in testing the activity of telomerase inhibitory compounds is described in various publications including WO 01/18015. In addition, the following kits are available commercially for research purposes for measuring telomerase activity: TRAPeze® XK Telomerase Detection Kit (Cat. s7707; Intergen Co., Purchase N.Y.); and Telo TAGGG Telomerase PCR ELISA plus (Cat. 2,013,89; Roche Diagnostics, Indianapolis Ind.).

A preferred protocol for measuring the ability of compounds to inhibit telomerase in a biochemical assay is the direct (non-PCR based) cell-free telomerase assay, referred to as the "Flashplate assay", and described in Asai et al., Cancer Research, 63:3931-3939 (2003).

The ability of compounds of the invention to inhibit telomerase in cells may be determined by incubating the compound with telomerase-expressing cells for a defined period of time, and then determining telomerase activity in a cytosolic extract. A preferred protocol for the cell-based assay is the cell-based telomerase assay described in Asai et al. (2003). Telomerase-expressing tumor cell lines that are suitable for such assays include HME50-5E human breast epithelial cells (provided by Dr. Jerry Shay, University of Texas Southwestern Medical Center), the ovarian tumor cell lines OVCAR-5 (MIISB, Milan) and SK-OV-3 (American Type Culture Collection, ATCC), human kidney carcinoma Caki-1 cells (Japanese Collection of Research Bioresources, JCRB), human lung carcinoma 1549 cells (ATCC), human epidermoid carcinoma A431 cells (JCRS), and human prostate cancer DU145 cells (ATCC).

F. Cell Proliferation Assays

A key therapeutic application of the compounds of the invention is the inhibition of the growth of telomerase-expressing cells, particularly tumor cells. Compounds of the invention that inhibit telomerase activity in cells will, like other known telomerase-inhibiting compounds, induce crisis in telomerase-positive cell lines, leading to cessation of cell growth and death. Importantly however, in normal human cells which do not express telomerase, such as BJ cells of fibroblast origin, no crisis or other toxicity is induced by treatment with the invention compounds. The ability of the compounds to specifically inhibit the growth of tumor cells can be assayed using tumor cell lines in vitro, or in xenograft animal models in vivo.

A preferred protocol for such growth curve assays is the short term cell viability assay described in Asai et al. (2003). In selecting a compound of the invention for therapeutic applications, it is preferred that the compound produce no significant cytotoxic effects at concentrations below about 10 μM in normal cells that do not express telomerase.

The ability of compounds of the invention to inhibit tumor cell growth in vivo can be confirmed using established xenograft models of human tumors, in which the test compound is administered either directly to the tumor site or systemically, and the growth of the tumor is followed by physical measurement. Animals treated with compounds of the invention are expected to have tumor masses that, on average, may increase for a period following the initial dosing, but will begin to shrink in mass with continuing treatment. In contrast, untreated control mice are expected to have tumor masses that continue to increase. A preferred example of a suitable in vivo tumor xenograft assay is described in Asai et al. (2003). Other examples are described in Scorski et al., Proc. Natl. Acad. Sci. USA, 94: 3966-3971 (1997) and Damm et al., EMBO J., 20:6958-6968 (2001).

G. Formulation of Invention Compounds

The present invention provides compounds that can specifically and potently inhibit telomerase activity, and which may therefore be used to inhibit the proliferation of telomerase-positive cells, such as tumor cells. A very wide variety of cancer cells have been shown to be telomerase-positive, including cells from cancer of the skin, connective tissue, adipose, breast, lung, stomach, pancreas, ovary, cervix, uterus, kidney, bladder, colon, prostate, central nervous system (CNS), retina and hematologic tumors (such as myeloma, leukemia and lymphoma).

Accordingly, the compounds provided herein are broadly useful in treating a wide range of malignancies. More importantly, the compounds of the present invention can be effective in providing treatments that discriminate between malignant and normal cells to a high degree, avoiding many of the deleterious side-effects present with most current chemotherapeutic regimens which rely on agents that kill dividing cells indiscriminately. Moreover, the compounds of the invention are more potent than equivalent unconjugated oligonucleotides, which means that they can be administered at lower doses, providing enhanced safety and significant reductions in cost of treatment. One aspect of the invention therefore is a method of treating cancer in a patient, comprising administering to the patient a therapeutically effective dose of a compound of the present invention. Telomerase inhibitors, including compounds of the invention, may be employed in conjunction with other cancer treatment approaches, including surgical removal of primary tumors, chemotherapeutic agents and radiation treatment.

For therapeutic application, a compound of the invention is formulated in a therapeutically effective amount with a pharmaceutically acceptable carrier. One or more invention compounds (for example, having different L or O components) may be included in any given formulation. The pharmaceutical carrier may be solid or liquid. Liquid carriers can be used in the preparation of solutions, emulsions, suspensions and pressurized compositions. The compounds are dissolved or suspended in a pharmaceutically acceptable liquid excipient. Suitable examples of liquid carriers for parenteral administration of the oligonucleotides preparations include water (which may contain additives, e.g., cellulose derivatives, preferably sodium carboxymethyl cellulose solution), phosphate buffered saline solution (PBS), alcohols (including monohydric alcohols and polyhydric alcohols, e.g., glycols) and their derivatives, and oils (e.g., fractionated coconut oil and arachis oil). The liquid carrier can contain other suitable pharmaceutical additives including, but not limited to, the following: solubilizers, suspending agents, emulsifiers, buffers, thickening agents, colors, viscosity regulators, preservatives, stabilizers and osmolarity regulators.

For parenteral administration of the compounds, the carrier can also be an oily ester such as ethyl oleate and isopropyl myristate. Sterile carriers are useful in sterile liquid form compositions for parenteral administration.

Sterile liquid pharmaceutical compositions, solutions or suspensions can be utilized by, for example, intraperitoneal injection, subcutaneous injection, intravenously, or topically. The oligonucleotides can also be administered intravascularly or via a vascular stent.

The liquid carrier for pressurized compositions can be a halogenated hydrocarbon or other pharmaceutically acceptable propellant. Such pressurized compositions may also be lipid encapsulated for delivery via inhalation. For administration by intranasal or intrabronchial inhalation or insufflation, the oligonucleotides may be formulated into an aqueous or partially aqueous solution, which can then be utilized in the form of an aerosol.

The compounds may be administered topically as a solution, cream, or lotion, by formulation with pharmaceutically acceptable vehicles containing the active compound.

The pharmaceutical compositions of this invention may be orally administered in any acceptable dosage including, but not limited to, formulations in capsules, tablets, powders or granules, and as suspensions or solutions in water or non-aqueous media. Pharmaceutical compositions and/or formulations comprising the oligonucleotides of the present invention may include carriers, lubricants, diluents, thickeners, flavoring agents, emulsifiers, dispersing aids or binders. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

While the compounds of the invention have superior characteristics for cellular and tissue penetration, they may be formulated to provide even greater benefit, for example in liposome carriers. The use of liposomes to facilitate cellular uptake is described, for example, in U.S. Pat. No. 4,897,355 and U.S. Pat. No. 4,394,448. Numerous publications describe the formulation and preparation of liposomes. The compounds can also be formulated by mixing with additional penetration enhancers, such as unconjugated forms of the lipid moieties described above, including fatty acids and their derivatives. Examples include oleic acid, lauric acid, capric acid, myristic acid, palmitic acid, stearic acid, linoleic acid, linolenic acid, dicaprate, tricaprate, recinleate, monoolein (a.k.a. 1-monooleoyl-rac-glycerol), dilaurin, caprylic acid, arichidonic acid, glyceryl 1-monocaprate, 1-dodecylazacycloheptan-2-one, acylcarnitines, acylcholines, mono- and di-glycerides and physiologically acceptable salts thereof (i.e., oleate, laurate, caprate, myristate, palmitate, stearate, linoleate, etc.).

Complex formulations comprising one or more penetration enhancing agents may be used. For example, bile salts may be used in combination with fatty acids to make complex formulations. Exemplary combinations include chenodeoxycholic acid (CDCA), generally used at concentrations of about 0.5 to 2%, combined with sodium caprate or sodium laurate, generally used at concentrations of about 0.5 to 5%.

Pharmaceutical compositions and/or formulations comprising the oligonucleotides of the present invention may also include chelating agents, surfactants and non-surfactants. Chelating agents include, but are not limited to, disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines). Surfactants include, for example, sodium lauryl sulfate, polyoxyethylene-9-lauryl ether and polyoxyethylene-20-cetyl ether; and perfluorochemical emulsions, such as FC-43. Non-surfactants include, for example, unsaturated cyclic ureas, 1-alkyl- and 1-alkenylazacyclo-alkanone derivatives, and non-steroidal anti-inflammatory agents such as diclofenac sodium, indomethacin and phenylbutazone.

Thus, in another aspect of the invention, there is provided a method of formulating a pharmaceutical composition, the method comprising providing a compound as described herein, and combining the compound with a pharmaceutically acceptable excipient. Preferably the compound is provided at pharmaceutical purity, as defined below. The method may further comprise adding to the compound, either before or after the addition of the excipient, a penetration enhancing agent.

The pharmaceutical composition will typically comply with pharmaceutical purity standards. For use as an active ingredient in a pharmaceutical preparation, a compound of this invention is generally purified away from other reactive or potentially immunogenic components present in the mixture in which they are prepared. Typically, to achieve pharmaceutical purity where a nucleic acid-based compound is the active ingredient, the active ingredient is provided in at least about 50% homogeneity, and more preferably 60%, 70%, 80% or 90% homogeneity, as determined by functional assay, chromatography, or gel electrophoresis. The active ingredient is then compounded into a medicament in accordance with generally accepted procedures for the preparation of pharmaceutical preparations. Thus, in the present invention, providing the compounds at pharmaceutical purity requires that the compound be provided at at least about 50% homogeneity, and more preferably at least 80% or 90% homogeneity.

The pharmaceutical composition will also typically be aliquoted and packaged in either single dose or multi-dose units. The dosage requirements for treatment with the oligonucleotide compound vary with the particular compositions employed, the route of administration, the severity of the symptoms presented, the form of the compound and the particular subject being treated.

Pharmaceutical compositions of the invention can be administered to a subject in a formulation and in an amount effective to achieve a clinically desirable result. For the treatment of cancer, desirable results include reduction in tumor mass (as determined by palpation or imaging; e.g., by radiography, radionucleotide scan, CAT scan, or MRI), reduction in the rate of tumor growth, reduction in the rate of metastasis formation (as determined e.g., by histochemical analysis of biopsy specimens), reduction in biochemical markers (including general markers such as ESR, and tumor-specific markers such as serum PSA), and improvement in quality of life (as determined by clinical assessment, e.g., Karnofsky score), increased time to progression, disease-free survival and overall survival.

The amount of compound per dose and the number of doses required to achieve such effects will vary depending on many factors including the disease indication, characteristics of the patient being treated and the mode of administration. Typically, the formulation and route of administration will provide a local concentration at the disease site of between 1 $\mu$M and 1 nM of the compound.

In general, the compounds are administered at a concentration that affords effective results without causing any harmful or deleterious side effects. Such a concentration can be achieved by administration of either a single unit dose, or by the administration of the dose divided into convenient subunits at suitable intervals throughout the day.

EXAMPLES

The following Examples illustrate the synthesis and activities of compounds of the invention in which the oligonucleotide component O is synthesized using the preferred thiophosphoramidate or phosphoramidate chemistries. In particular examples, lipid moieties are conjugated at either the 3' or 5' terminus, or both, either with or without a linker. The general structure of these compounds can be represented as:

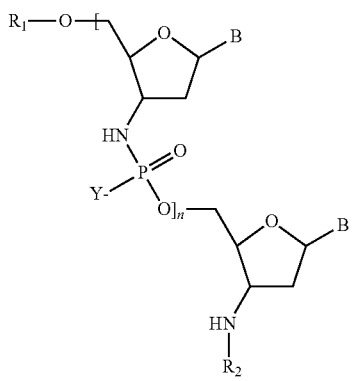

wherein $R_1$ and $R_2$ are independently either H or a lipid moiety (L), Y is O (phosphoramidate oligonucleotide) or S (thiophosphoramidate oligonucleotide), n is an integer, typically between 4 and 49, and B represents a base (independently selected for each nucleoside subunit). The optional linker is not depicted in this structure.

Example 1

Synthesis of Compounds

A. General Methods

Oligonucleotide N3'→P5' phosphoramidates (NP) and thiophosphoramidates (NPS) were synthesized on a 1 µmole scale using the amidite transfer reaction on an ABI 394 synthesizer according to the procedures described by McCurdy et al., (1997) Tetrahedron Letters, 38:207-210 and Pongracz & Gryaznov, (1999) Tetrahedron Letters 49:7661-7664, respectively. The fully protected monomer building blocks were 3'-aminotrityl-nucleoside-5'-(2-cyanoethyl-N,N-diisopropylamino)nucleosidephosphoramidites, specifically 3'-deoxy-thymidine, 2',3'-dideoxy-$N^2$-isobutyryl-guanosine, 2',3'-dideoxy-$N^6$-benzoyl-adenosine, and 2',3'-dideoxy-$N^4$-benzoyl-cytidine purchased from Transgenomic, Inc. (Omaha, Nebr.). 3'-aminotrityl-5'-succinyl-nucleosides were coupled with amino group containing long chain controlled pore glass (LCAA-CPG) and used as the solid support. The synthesis was performed in the 5' to 3' direction. Oligonucleotides with NP backbones were synthesized using the standard 1 µM (ABI Perkin Elmer) procedure with an iodine/$H_2O$ oxidation step, while oligonucleotides with NPS backbones were prepared using the sulfur protocol in which a 0.1 M solution of phenylacetyl disulfide (PADS) in an acetonitrile: 2,6-lutidine 1:1 mixture was used as the sulfurization reagent. Coupling time was 25 seconds for preparation of both types of backbone. An 18:1:1 mixture of THF:isobutyric anhydride: 2,6-lutidine was used as the capping agent. Three methods were used to conjugate the lipid moiety to the oligonucleotide: method (i) coupling using phosphoramidite reagents on the synthesizer to introduce the lipid moiety at the 3' end; method (ii) use of a modified solid support (exemplified in Schematic C above) to which the lipid group was conjugated prior to initiation of elongation synthesis for production of 5' conjugates; and method (iii) reaction of the free 3'-amino group while still on the solid support followed by deprotection. Further details of these methods are provided below. Oligonucleotides were deprotected with concentrated ammonia for lipid groups attached to the 3' terminus or a nucleobase, or a 1:1 mixture of ethanol:concentrated ammonia for lipid groups attached to the 5' terminus, at 55° C. for 6-8 hrs. The crude products were either desalted on Pharmacia NAP-25 gel filtration columns or precipitated with ethanol from 1 M sodium chloride then lyophilized in vacuo.

The oligonucleotide products were subsequently purified by reversed phase HPLC using a Beckman Ultrasphere C18 (5µ) 250×10 mm column. The products were eluted with a linear gradient of acetonitrile in 50 mM triethylammonium acetate at a flow rate of 2 ml/min and converted to sodium salt with precipitation from 1 M sodium chloride with neat cold ethanol. Purity of the compounds was assessed by analytical RP HPLC using the above solvent system and by PAGE. $^1$H and $^{31}$P NMR spectra were recorded on a VARIAN Unity Plus 400 MHz instrument and electrospray ionization mass spectra (ESI MS) were obtained using a WATERS Micromass ZMD mass spectrometer.

B. Conjugation of Lipid Groups to the Oligonucleotide

As noted above, various methods may be employed to conjugate the lipid groups to the oligonucleotide. Details of specific methods are as follows:

Method (i) In this method phosphoramidite reagents containing a conjugated lipid group are added as the 3' nucleoside during the oligonucleotide synthesis process, resulting in lipid group conjugated to the 3' terminus of the oligonucleotide. The synthesis and subsequent coupling of two fatty acid-containing phosphoramidites exemplify this approach.

(i/a) Synthesis and Coupling of 3-Palmitoylamino-Propane-1-O-(2-Cyanoethyl-N,N-Diisopropylphosphoramidite).

To 1.0 g (13.3 mmole) 3-amino-propanol dissolved in acetonitrile-methylene chloride 1:4 mixture (400 ml), 10 ml of diisopropylethylamine and 4.06 ml (13.3 mmole) palmitoyl chloride were added. After stirring the reaction overnight more methylene chloride was added and the mixture was then sequentially washed with saturated sodium bicarbonate, brine, and water. The organic phase was dried over sodium sulfate and evaporated to dryness. 500 mg (1.6 mmole) of the white solid obtained was azeotroped by coevaporation with dry acetonitrile and dissolved in 50 ml methylene chloride. After the addition of 1.1 ml diisopropylethylamine (4 eq.), 390 µl (1.7 mmole) 2-cyanoethyl diisopropylchlorophosphoramidite was added dropwise. The reaction mixture was stirred for 1 hr to give a clear solution. The reaction mixture was sequentially washed with saturated sodium bicarbonate and brine, dried over sodium sulfate and evaporated to dryness. The product was purified by silica get chromatography using ethylacetate:methylene chloride:triethylamine 45:45: 10 v/v solvent system. The 0.7 g (90%) wax-like solid was dried in a desiccator over $P_2O_5$ before use on the DNA synthesizer. $^{31}$P NMR (CDCl$_3$) 148.45 ppm, ES MS (MH$^+$) 514. For coupling on the DNA synthesizer, a 0:1 M solution was prepared in anhydrous acetonitrile-methylene chloride 9:1 mixture. This synthesis results in the reagent used for production of the conjugated oligonucleotide depicted in FIG. 1D.

(i/b) Synthesis and Coupling of 3-Palmitoylamino-1-Hydroxy-Propane-2-O-(2-Cyanoethyl-N,N-Diisopropylphosphoramidite).

1 g (10.97 mmole) 3-amino-propanediol was suspended in 10 ml of pyridine, and 3.017 g (10.97 mmole) palmitoyl chloride in 2 ml of DMF was added dropwise with vigorous stirring. After 15 minutes of stirring the gel was filtered and air-dried. The solid was recrystallized from hot ethanol and hot 2-propanol as a white powder. The white solid was co-evaporated with pyridine, then dissolved in 30 ml dry pyridine. 2.89 g (8.55 mmole) DMT-chloride was added and the reaction mixture stirred for 30 minutes, with the reaction being followed by TLC. After quenching with methanol, the pyridine was evaporated and the reaction was worked up from methylene chloride-saturated sodium bicarbonate. The resulting oil was purified by silica gel column chromatography using 4:1 hexane/ethyl acetate as the eluent. The 2.4 g (3.64 mmole) yellow oil obtained was azeotroped with pyridine, dissolved in 100 ml methylene chloride and 4 eq diisopropylethylamine (2.5 ml). To the stirred solution 920 µl (4 mmole) 2-cyanoethyl diisopropylchlorophosphoramidite was added dropwise. The reaction was followed by TLC and was found to be complete after 2 hr and worked up as above. The product was purified by silica gel chromatography using an ethylacetate:methylene chloride:triethylamine 45:45:10 solvent system. The obtained solid was dried in a desiccator before use on the DNA synthesizer (0.1 M solution in acetonitrile). $^{31}$P NMR (CDCl$_3$) 149.9, 150.2 ppm, ES MS (MNa$^+$) 854.57. This synthesis results in the reagent used for the production of the conjugated oligonucleotide depicted in FIG. 1 AA.

Method (ii) In this method, a modified solid support conjugated to the lipid moiety is used as the starting point for the 5' to 3' synthesis of the oligonucleotide, resulting in a 5' conjugate. The synthesis and use of two modified solid supports exemplify this approach.

(ii/a) Synthesis of 3-Palmitoylamino-1-Dimethoxytrityloxy-2-Succinyloxy-Propane 1 g (10.97 mmole) of 3-amino-1,2-propanediol was suspended in 10 ml of pyridine. 3.017 g (10.97 mmole) palmitoyl chloride in 2 ml of DMF was added dropwise with vigorous stirring. After 15 minutes of stirring, the gel was filtered and air-dried. The solid was recrystallized from hot ethanol and hot 2-propanol as a white powder. The white solid was co-evaporated with pyridine, then dissolved in 30 ml dry pyridine. 3.2 g (9.46 mmole) DMT-chloride was added and the reaction mixture stirred for 30 minutes with the reaction being followed by TLC. After quenching with methanol, the pyridine was evaporated and the reaction was worked up from methylene chloride-sat. sodium bicarbonate. The resulting oil was purified by silica gel column chromatography using 4:1 hexane/ethyl acetate as the eluent. The 2.5 g (3.95 mmole) yellow oil obtained was dissolved in 30 ml methylene chloride, and then 475 mg succinic anhydride and 483 mg dimethylaminopyridine were added and the reaction mixture stirred for 1 hour. The reaction was monitored by TLC and more succinic anhydride was added if needed. The methylene chloride solution was washed with cold sodium citrate buffer (pH=4) and the organic phase dried over sodium sulfate than evaporated to dryness. The end product obtained was 2.0 g (24.9%).

(ii/b) Synthesis of 3-Stearoylamino-1-Dimethoxytrityloxy-2-Succinyloxy-Propane 1 g (10.97 mmole) of 3-amino-propanediol was suspended in 10 ml of pyridine. 3.32 g (10.97 mmole) stearoyl chloride in 10 ml of DMF was added dropwise with vigorous stirring. After 15 minutes of stirring, the gel was filtered and air-dried. The solid was recrystallized from hot ethanol and hot 2-propanol as a white powder. The white solid was co-evaporated with pyridine, then dissolved in 30 ml dry pyridine. 2.89 g (8.55 mmole) DMT-chloride was added and the reaction mixture stirred for 30 minutes with the reaction being followed by TLC. After quenching with methanol, the pyridine was evaporated and reaction was worked up from methylene chloride-sat. sodium bicarbonate. The resulting oil was purified by silica gel column chromatography using 4:1 hexane/ethyl acetate as the eluent. The 2.4 g (3.64 mmole) yellow oil obtained was dissolved in 30 ml methylene chloride, and then 437 mg succinic anhydride and 444 mg dimethylaminopyridine were added and the reaction mixture stirred for 1 hour. The reaction was monitored by TLC and more succinic anhydride was added if needed. The methylene chloride solution was washed with cold sodium citrate buffer (pH=4) and the organic phase dried over sodium sulfate than evaporated to dryness. The endproduct obtained was 1.2 g (14.4%).

The products synthesized in (ii/a) and (ii/b) were then conjugated to long chain amino controlled pore glass (LCAA-CPG) to produce the modified solid support, as follows:

In a 100 ml peptide synthesis vessel, 20 g of LCAA-CPG (Transgenomic, Inc., ~200 mmole/g —NH$_2$ loading) were washed with dry dimethylformamide. In a separate flask 5.55 mmole of the products described in (ii/a) or (ii/b) above were dissolved in 40 ml chloroform, 3 ml diisopropylethylamine, and 2.13 g (8.3 mmole) 2-chloro-1-methylpyridinium iodide was added. This suspension was poured over the dry CPG in the peptide synthesis vessel (with the stopcock open) until the solution soaked in approximately halfway through the CPG. Then the stopcock and the upper cap were closed and the vessel shaken until the solution covered the CPG completely. (If necessary more chloroform can be added, but the volume should be kept to a minimum.) The vessel was then placed on a shaker and the reaction allowed to proceed overnight at room temperature. The CPG was filtered, and then washed with methylene chloride, methanol and acetonitrile. The unreacted amino groups were capped using a 1:1 solution of THF-2,6-lutidine-isobutyric anhydride 18:1:1 and Cap B (N-methylimidazole/THF) for 1 hour at room temperature on a shaker. After further filtration, the beads were washed with methanol, methylene chloride and acetonitrile. The loading was determined by the standard method of measuring the dimethoxytrityl cation absorbance at 498 nm of a sample deblocked using methanolic perchloric acid and was found to be 50-60 µmole/g.

Once the modified solid supports were produced, they were employed in oligonucleotide syntheses as described above. Examples of the oligonucleotide conjugates produced in this way are shown in FIGS. 1F, 1G and 1H.

Method (iii) In this method, synthesis of the oligonucleotide is completed and while it remains fully protected and bound to the solid support, the 3' terminus is reacted with an acid anhydride (iii/a), anhydride (iii/b), acid (iii/c) or aldehyde (iii/d) form of the lipid group, as follows.

(iii/a) Solid support bound fully protected oligonucleotide containing free 3'-amino group (4 µmole) was dried in vacuo and suspended in 3 ml anhydrous chloroform. After the addition of 140 µl (0.8 mmole) diisopropylethylamine and 0.4 mmole of the appropriate acid chloride (122 µl palmitoyl chloride for example) the mixture was shaken for 2 minutes and quickly filtered, then washed with chloroform, methanol and acetonitrile. The dry beads were suspended in 1-2 ml concentrated ammonium hydroxide and heated for 5 hours at 55° C. The cooled ammonium hydroxide solution was then filtered and evaporated. The lipid conjugate product was isolated by HPLC. Using the conditions described above the product eluted around 40 minutes. After evaporation the product was precipitated from 1 M sodium chloride and ethanol to give the sodium salt.

(iii/b) To the dry solid support bound fully protected oligonucleotide (1 μmole) 0.1 mmole of the appropriate anhydride and 170 μl diisopropylethylamine dissolved in 2 ml chloroform were added and the vial containing the mixture was placed on a shaker overnight. After filtration, the beads were washed with chloroform, methanol and acetonitrile and the conjugated oligonucleotide was deblocked and purified as above.

(iii/c) 1 μmole solid support bound fully protected oligonucleotide was reacted on a shaker with a solution of 0.1 mmole of the suitable acid, 25 mg 2-chloro-1-methylpyridinium iodide (0.1 mmole) and 170 μl disopropylethylamine in 2 ml chloroform overnight. Washing, deblocking and purification were performed as described above.

(iii/d) A solution of 0.3 mmole of the desired aldehyde, 31.5 mg sodium cyanoborohydride, and 100 μl 0.5 M sodium acetate in 2 ml tetrahydrofuran were added to 1 μmole solid support bound fully protected oligonucleotide and placed on a shaker for 30 minutes. Washing, deblocking and purification were performed as described above.

Figure 2E:
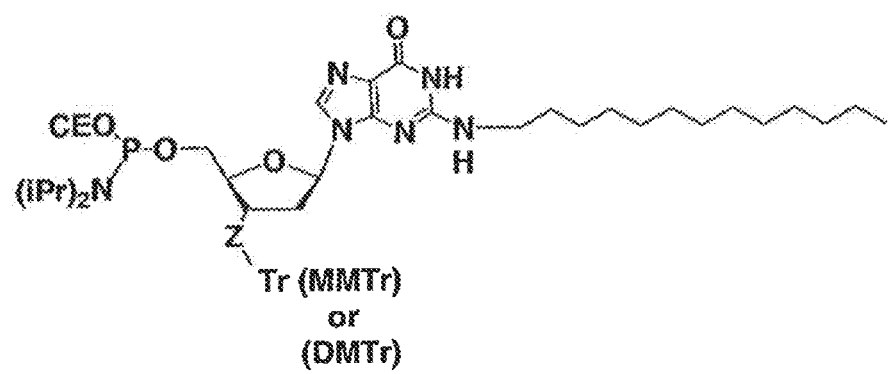
FIG. 2E shows an exemplary protected base modified with a lipid group (in this case, guanosine modified by conjugation to tetradecyl), which can be used in standard oligonucleotide synthesis procedures to prepare an oligonucleotide in which one or more lipid groups are covalently attached to one or more nucleobase.

Method (iv) In this method, the lipid group is conjugated not to a terminus of the oligonucleotide, but to a nucleobase on the chain, for example a guanosine. These compounds are synthesized using a conventional oligonucleotide chain extension protocol, as described above, but with the incorporation of a base modified with a covalently conjugated lipid group, such as depicted in FIG. 2E. Examples of compounds in which the lipid group is conjugated to a nucleobase are shown in FIGS. 1Q and R.

Example 2

Activity of Compounds in Biochemical and Cell-Based Assays

Conjugated oligonucleotides as described herein were tested for their ability to inhibit telomerase in the biochemical Flashplate assay and the cell-based assay, as described above and in Asai et al. (2003). The results are presented in the following table. In this table, the following abbreviations are used:

Oligonucleotide Sequences:
1=TAGGGTTAGACAA, complementary to bases 42-54 of hTR, SEQ ID NO:1
2=CAGTTAGGGTTAG, complementary to bases 38-50 of hTR, SEQ ID NO:1

Chemistry:
NP indicates that the oligonucleotide has phosphoramidate internucleoside linkages
NPS indicates that the oligonucleotide has thiophosphoramidate internucleoside linkages Conjugate:
5' indicates that the lipid moiety is conjugated to the 5' terminus of the oligonucleotide
3' indicates that the lipid moiety is conjugated to the 3' terminus of the oligonucleotide Human Cancer Cell Types (all Available from ATCC):
HT-3 and A431: cervical carcinoma
U-251: glioblastoma multiforme
DU145 and LNCaP: prostate cancer
Caki: renal clear cell carcinoma
NCIH522: lung adenocarcinoma
Ovcar-5: ovarian carcinoma
Hep3B: hepatocellular carcinoma

| Oligonucleotide sequence | Chemistry | Conjugated lipid group (FIG. 1 reference) | IC50 (nM) in biochemical assay | IC50 (uM) in cell assay (cell type) |
|---|---|---|---|---|
| 1 | NPS | none | 0.15 | 1.6 (HT-3) |
| | | | | 0.79 (A431) |
| | | | | 6.3 (U-251) |
| | | | | 1.4 (DU145) |
| | | | | 2.99 (Caki) |
| | | | | 6.5 (Hep3B) |
| 1 | NPS | 3'-myristoylamide (1A) | 0.8 (+/−0.2) | 0.35 (Caki) |
| | | | | 0.21 (HT-3) |
| 1 | NPS | 3'-palmitoylamide (1B) | 2.9 (+/−2.2) | 0.21 (A431) |
| | | | | 0.37 (HT-3) |
| | | | | 0.19 (LNCaP) |
| | | | | 0.2 (NCl-H522) |
| | | | | 0.65, 0.49 (U-251) |
| | | | | 2.84 (Hep3B) |
| | | | | 1.97 (Ovcar5) |
| 1 | NPS | 3'-stearoylamide (1C) | 11.9 (+/−10.5) | 0.13, 0.28 (HT-3) |
| | | | | 0.2 (NCl-H522) |
| 1 | NPS | 3'-palmitoylamido-propyl-thiophosphate (1D) | 0.48 (+/−0.3) | 0.27 (HT-3) |
| 1 | NPS | 3'-thioctylamide (1BB) | 1.19 (+/−0.7) | N/D |
| 1 | NPS | 3'-lysyl-bis-stearoylamide (1E) | 2.45 (+/−0.7) | 2.98 (HT-3) |
| 1 | NPS | 3'-oleinylamide (1M) | 5.2 (+/−0.8) | 1.16 (HT-3) |
| 1 | NPS | 3'-linoleylamide (1O) | 3.9 | 1.25 (HT-3) |
| 1 | NPS | 3'-bis-decyl (1K) | 36.5 (+/−8.9) | N/D |
| 1 | NPS | 3'-bis-dodecyl (1J) | >100 | N/D |
| 1 | NPS | 3'-palmitoylamido-aminoglycerol-thiophosphate (1AA) | 0.4 (+/−0.14) | 0.5 (HT-3) |

-continued

| Oligonucleotide sequence | Chemistry | Conjugated lipid group (FIG. 1 reference) | IC50 (nM) in biochemical assay | IC50 (uM) in cell assay (cell type) |
|---|---|---|---|---|
| 1 | NPS | 3'-trityl (1P) | 0.9 (+/−0.01) | >10 (HT-3) |
| 1 | NPS | 5'-palmitoylamido-glycerol-thiophosphate, 3'-palmitoylamide (not shown in FIG. 1) | >100 | 17.5 (HT-3) |
| 1 | NPS | 5'-palmitoylamido-aminoglycerol-thiophosphate (1F) | 5.01 (+/−3.37) | 0.36, 0.22 (HT-3) 0.15 (DU145) 0.16 (U-251) 3.02 (Hep3B) 0.92 (Ovcar5) |
| 1 | NPS | 5'-OH-palmityl-thiophosphate (1X) | 3.6 | |
| 1 | NPS | 5'-stearoylamido-aminoglycerol-thiophosphate (1H) | 5.2 (+/−4.1) | N/D |
| 1 | NPS | 5'-cholesterylamido-aminoglycerol-thiophosphate (1CC) | 2.6 (+/−0.14) | 0.25 (HT-3) |
| 1 | NPS | 5'-palmitoylamido-aminoglycerol-thiophosphate (1G) | 4.65 (+/−0.35) | 0.55 (HT-3) |
| 1 | NPS | 5'-C11-teflon-thiophosphate (1U) | 4.15 (+/−1.91) | 0.14 (HT-3) |
| 1 | NPS | 5'-C13-teflon-thiophosphate (1V) | | 0.23 (HT-3) |
| 1 | NPS | 5'-batyl-thiophosphate (1Y) | | 0.59 (HT-3) |
| 1 | NPS | 5',3'--bis-palmitoylamido-glycerol thiophosphate (not shown on Figure) | 0.3 (+/−0.14) | 0.34 (HT-3) |
| 1 | NPS | 3'-palmitoylamido-aminoglycerol-thiophosphate (1AA) | 0.4 (+/−0.14) | 0.52 |
| 1 | NP | none | 0.8 | 30 |
| 1 | NP | 3'-palmitoylamide (1B) | 2.85 (+/−1.06) | N/D |
| 1 | NP | 3'-dodecyl (1I) | 3.2 (+/−0.57) | N/D |
| 1 | NP | 3'-bis dodecyl (1J) | >100 | N/D |
| 1 | NP | 3'-bis decyl (1K) | >100 | N/D |
| 1 | NP | 3'-cholesterylamido-aminoglycerol-thiophosphate (1S) | >10 | 3.6 (HT-3) |
| 1 | NP | 5'-palmitoylamido-aminoglycerol-thiophosphate (1F) | 6.25 (+/−2.33) | 6.5 (HT-3) |
| 1 | NP | 5'-stearoylamido-aminoglycerol-thiophosphate (1H) | 2.4 (+/−1.13) | 3.02 (HT-3) |
| 1 | NP | 5'-cholesterylamido-aminoglycerol-thiophosphate (1CC) | >10 | 0.8 (HT-3) |
| 1 | NP | 3'-lysyl-bis-stearoylamide (1E) | 50 | |

Example 3

Comparative Potency and Bioavailability Studies

Two compounds of the invention, along with a non-conjugated oligonucleotide, were selected for separate detailed studies. The selected compounds, depicted in FIG. 9, were as follows:

Compound A (Non-Conjugated): a thiophosphoramidate oligonucleotide of sequence TAGGGTTAGACAA (this sequence is complementary to bases 42-54 of hTR, SEQ ID NO:1) (FIG. 9A).

Compound B: the oligonucleotide of compound A conjugated to 3' palmitoylamide (FIG. 9B).

Compound C: the oligonucleotide of compound A conjugated to 5'-palmitoylamido-glycerol-thiophosphate (FIG. 9C).

Studies on these compounds are reported in this and the following Examples.

The following table shows the melting temperatures of each of these three compounds when associated with matched RNA (determined using standard methods), the $IC_{50}$ value for telomerase inhibition determined using the biochemical assay, and the $IC_{50}$ for telomerase inhibition determined using the cell-based assay (with HT-3 cells) as described above.

| Compound | Duplex Tm (° C.) | IC$_{50}$ (nm) biochemical assay | IC$_{50}$ (um) cell-based assay |
|---|---|---|---|
| A | 70 | 0.15 | 1.6 |
| B | 66.5 | 1.7 | 0.16 |
| C | 65.5 | 0.9 | 0.11 |

As shown in the table, the non-conjugated oligonucleotide A showed very high affinity binding to its target, with a melting temperature of 70° C., and an IC$_{50}$ value for telomerase inhibition of 0.15 nM in a biochemical assay (where cellular uptake is not an issue). Although compound A had good uptake into intact cells, with a low micromolar IC$_{50}$ for telomerase inhibition in multiple different tumor cell lines (1.6 μM in HT-3 cells in this experiment), this reflected an approximately 10,000-fold loss of potency in intact cells relative to biochemical potency. The addition of the lipid group to either the 5' or 3' end of the oligonucleotide (compounds C and B, respectively) modestly reduced the Tm, which still remained very high at 65.5-66.5° C., and reduced the biochemical potency 6 to 11-fold compared to the non-conjugated compound A. Of critical importance, however, the potency of the lipid-conjugated compounds B and C in intact cells was reduced by only ~100-fold compared to the biochemical potency of these compounds. As a result of greater cellular uptake, compounds B and C demonstrated at least 10-fold higher potency in the HT-3 cells compared to the non-conjugated oligonucleotide (compound A).

Similar results were observed with other types of human cancer cells. FIGS. 3 and 4, show data obtained with compounds A, B and C in intact U251 (human glioblastoma) cells and DU145 (human prostate cancer) cells, respectively. The IC$_{50}$ of compound C (5' lipidated form) was approximately 10-fold lower than that of compound A in the U251 cells, and approximately 38 fold lower in the DU145 cells, confirming the increased efficacy of treatment with compound C.

Example 4

Inhibition of Telomerase Activity in Human Tumors in Animal Models

The abilities of the non-conjugated oligonucleotide compound A and the lipid-conjugated oligonucleotide compound C to inhibit telomerase in tumors growing in animals were compared in the following experiment. Athymic (nu/nu) mice were inoculated with DU-145 tumor cells in both flanks. When the tumors (two tumors/mouse) reached 50-100 mm$^3$ in size, the mice received a single tail vein injection of PBS, FITC-labeled compound A, or FITC-labeled compound C (both compounds administered at 40 mg/kg). Mice were sacrificed 24 hours post IV injection; one tumor was harvested for fluorescent imaging and the other tumor was analyzed for telomerase activity by TRAP assay.

The levels of fluorescence were comparable in both treatment groups. However, as shown in FIG. 5, compound C resulted in greater inhibition of telomerase activity than did compound A. The vertical arrows in the lanes corresponding to 0.75 ug of tumor lysate indicate that these samples contain comparable levels of the internal standard (indicated by the horizontal arrow). Blood contains hemoglobin and other non-specific taq polymerase inhibitors (used in PCR amplification of the telomerase products), as indicated by the loss of the internal standard in the lanes at the left of the gel. However, these non-specific inhibitors can be diluted out by serial dilutions (decreasing amounts of tumor lysate in the reaction mixture). At the lowest concentration of tumor lysate (the three lanes on the right), where the internal standard is comparable in all three treatment conditions, it is clear that compound C inhibited telomerase activity to a greater extent than did a comparable dose of compound A.

Example 5

Reduction of Myeloma Protein Levels in Animal Models

The plasma of patients with myeloma contains a characteristic high level (detected as a "myeloma spike" or M-protein) of the antibody produced by the cancerous cells. Reduction of the M-protein level is correlative with remission of the disease. In this experiment, the abilities of the non-conjugated oligonucleotide compound A and the lipid-conjugated oligonucleotide compound C to reduce the level of the level of M-protein in animals injected with myeloma cells were compared. Irradiated NOD/SCID mice were injected with 10$^6$ CAG myeloma cells and then treated with intraperitoneal (IP) injections of PBS, compound A in PBS, or compound C in PBS. Compound A was dosed at 25 mg/kg/day (175 mg/kg week×5 weeks); compound C was dosed at 25 mg/kg/day for the first 2 weeks, held for week three, and then dosed at 25 mg/kg/day three days per week for the last two weeks (average dose of 100 mg/kg/week over the five weeks). At the end of treatment (35 days after inoculation) the mice were sacrificed, and the plasma pooled within each group (4-5 mice/group) for determination of myeloma protein. As shown in FIG. 6, despite a 40% lower dose of compound C (cumulative dose of 500 mg vs 875 mg for compound A), the compound C group demonstrated a lower level of myeloma protein (values normalized per mouse).

Example 6

Inhibition of Human Tumor Growth in Animal Models

The abilities of the non-conjugated oligonucleotide compound A and the lipid-conjugated oligonucleotide compound C to inhibit growth of human tumors in animals were compared in the following experiment. Irradiated NOD/SCID mice were inoculated subcutaneously with CAG myeloma cells, and after 14 days of tumor growth were treated with IP injections of PBS, compound A (25 mg/kg/day M-F, or 125 mg/kg/week) or compound C (25 mg/kg MWF, or 75 mg/kg/week). As shown in FIG. 7, despite a 40% lower dose, compound C demonstrated greater anti-tumor efficacy than compound A. (In this study, compound A was administered at a 30% lower dose than had previously been associated with anti-tumor efficacy in this model, 175 mg/kg/week).

As part of this study, the flank CAG myeloma tumors were excised post-sacrifice and analyzed for telomerase activity (by TRAP assay) and TRF length by Southern blot. As shown in FIG. 8, despite being administered at a 40% lower dose, compound C demonstrated substantially greater inhibition of telomerase activity (83% reduction) and induction of telomere shortening in the tumor cells (2.85 Kb mean TRF). The higher dose of compound A afforded less telomerase inhibition (41%), and did not result in significant telomere shortening over the time course of the study.

The subject matter provided in this disclosure can be modified as a matter of routine optimization, without departing from the spirit of the invention, or the scope of the appended claims.

We claim:

1. A telomerase inhibitory compound comprising the structure:

O-(x-L)n, wherein:

O is an oligonucleotide comprising a sequence consisting of
GTTAGGGTTAG;
GTTAGGGTTAGAC;
GTTAGGGTTAGACAA;
GGGTTAGAC;
CAGTTAGGG; or
CAGTTAGGGTTAG;
  wherein the internucleoside linkages of the oligonucleotide O are N3'→P5' thiophosphoramidate linkages;
  x is an optional linker;
  L is a lipid moiety; and
  n=1 or 2 wherein each (x-L) component is independently covalently conjugated to the 5' terminus or the 3' terminus of the oligonucleotide O and wherein if n>1, each (x-L) component is independently selected; or a pharmaceutically acceptable salt thereof.

2. A compound of claim 1 wherein x comprises an amide bond, a glycerol or an aminoglycerol linker optionally linked to the oligonucleotide O through a 5'- or 3'-linked phosphate group.

3. A compound of claim 2 wherein L is a lipid selected from the group consisting of substituted and unsubstituted fatty acids and sterols.

4. A compound of claim 3 wherein L is a fatty acid substituted with fluorine.

5. A compound of claim 2 wherein L is a substituted or unsubstituted hydrocarbon.

6. A compound of claim 5 wherein L is a hydrocarbon substituted with fluorine.

7. A compound of claim 1 wherein n=1 and the x-L component is covalently conjugated to the 5' terminus of the oligonucleotide O.

8. A compound of claim 1 wherein n=1 and the (x-L) component is covalently conjugated to the 3' terminus of the oligonucleotide O.

9. A compound of claim 1 wherein n=2, one independently selected (x-L) component is covalently conjugated to the 5' terminus and one independently selected (x-L) component is covalently conjugated to the 3' terminus.

10. A compound of claim 9 wherein each (x-L) is palmitoylamido-aminoglycerol-thiophosphate.

11. A telomerase inhibitory compound comprising the structure:

O-(x-L)n, wherein:

O is TAGGGTTAGACAA
  wherein the internucleoside linkages of the oligonucleotide O are N3'→P5' thiophosphoramidate linkages;
  wherein n=1 or 2, wherein if n>1, each (x-L) component is independently selected, and
wherein (x-L) is selected from the group consisting of 3'-myristoylamide, 3'-palmitoylamide, 3'-stearoylamide, 3'-palmitoylamido-propyl-thiophosphate, 3'-oleinylamide, 3'-linoleylamide, 5'-cholesterylamido-aminoglycerol-thiophosphate, 5'-C11-teflon-thiophosphate, 5'-C13-teflon-thiophosphate, 5'-batyl-thiophosphate, 3'-palmitoylamido-aminoglycerol-thiophosphate, 5'-palmitoylamido-bis-aminoglycerol-thiophosphate, 3'-cholesterylamido-aminoglycerol-thiophosphate, 5'-stearoylamido-aminoglycerol-thiophosphate; or a pharmaceutically acceptable salt thereof.

12. A compound of claim 11 wherein n=1.

13. A compound of claim 12 wherein L is directly linked to the 3' terminus of the oligonucleotide L through an amide bond.

14. A compound of claim 12, comprising the following structure:

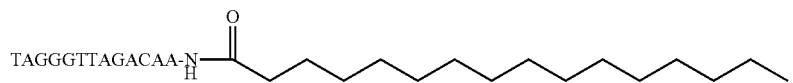

or a pharmaceutically acceptable salt thereof.

15. A compound of claim 1 wherein each (x-L) component is independently selected from the group consisting of 3'-myristoylamide, 3'-palmitoylamide, 3'-stearoylamide, 5'-cholesterylamido-aminoglycerol-thiophosphate, 5'-palmitoylamido-aminoglycerol-thiosphosphate, 3'-palmitoylamido-aminoglycerol-thiophosphate, 3'-palmitoylamido-propyl-thiophosphate, 3'-oleinylamide, 3'-linoleylamide, 5'-C11-teflon-thiophosphate, 5'-C13-teflon-thiophosphate, 5'-palmitoylamido-bis-aminoglycerol-thiophosphate, 3'-cholesterylamido-aminoglycerol-thiophosphate, 5'-stearoylamido-aminoglycerol-thiophosphate and 5'-batyl-thiophosphate.

* * * * *